United States Patent
Homan et al.

(10) Patent No.: US 8,175,559 B2
(45) Date of Patent: May 8, 2012

(54) RECEIVING APPARATUS

(75) Inventors: Masatoshi Homan, Hino (JP); Ayako Nagase, Hachioji (JP); Seiichiro Kimoto, Hachioji (JP); Kazutaka Nakatsuchi, Hino (JP); Manabu Fujita, Hino (JP); Akira Matsui, Hino (JP); Toshiaki Shigemori, Hachioji (JP)

(73) Assignees: Olympus Corporation (JP); Olympus Medical Systems, Corp. (JP)

( * ) Notice: Subject to any disclaimer, the term of this patent is extended or adjusted under 35 U.S.C. 154(b) by 924 days.

(21) Appl. No.: 11/571,418

(22) PCT Filed: Aug. 29, 2006

(86) PCT No.: PCT/JP2006/317007
§ 371 (c)(1),
(2), (4) Date: Aug. 27, 2008

(87) PCT Pub. No.: WO2007/029570
PCT Pub. Date: Mar. 15, 2007

(65) Prior Publication Data
US 2008/0318540 A1    Dec. 25, 2008

(30) Foreign Application Priority Data

Sep. 9, 2005 (JP) ................................. 2005-262045
Oct. 20, 2005 (JP) ................................. 2005-306116
Oct. 26, 2005 (JP) ................................. 2005-311663

(51) Int. Cl.
*H04B 17/02* (2006.01)
(52) U.S. Cl. ............... 455/133; 455/195.1; 455/146; 455/41.2; 455/282
(58) Field of Classification Search ........... 455/63.1, 455/67.11, 133, 195.1, 41.2, 279.1, 282
See application file for complete search history.

(56) References Cited

U.S. PATENT DOCUMENTS
6,437,577 B1 * 8/2002 Fritzmann et al. ............ 324/523
(Continued)

FOREIGN PATENT DOCUMENTS
JP          09-218233          8/1997
(Continued)

OTHER PUBLICATIONS
International Search Report PCT/JP2006/317007 dated Nov. 20, 2006 (Japanese Patent Office).
(Continued)

*Primary Examiner* — Yuwen Pan
(74) *Attorney, Agent, or Firm* — Ostrolenk Faber LLP

(57) ABSTRACT

The present invention is intended to be able to ensure detecting whether an open-circuit occurs to a feeder within short time with simple configuration. A receiving apparatus 2 according to the present invention receives image information transmitted from a capsule endoscope 3 through a coaxial cable and a receiving antenna selected and switched to from among coaxial cables 9a to 9d connected to receiving antennas 8a to 8d, respectively by a changeover switch 20. The receiving apparatus 2 includes a changeover switch 22, an open-circuit detecting circuit 23, and a control unit 26. The changeover switch 22 branches the coaxial cables 9a to 9d near the changeover switch 20, and selects and switches to one of the branched coaxial cables. The open-circuit detecting circuit 23 applies a direct-current voltage to the coaxial cable selected by the changeover switch 22 through a constant-current source 203, and detects whether an open-circuit occurs to the coaxial cable by determining whether a voltage of the coaxial cable is grounded. The control unit 26 controls the changeover switch 22 to perform selection/switching, and controls the open-circuit detecting circuit 23 to perform open-circuit detection synchronously with the selection/switching control over the changeover switch 22.

7 Claims, 19 Drawing Sheets

U.S. PATENT DOCUMENTS

2006/0128337 A1 6/2006 Fujita et al.

FOREIGN PATENT DOCUMENTS

| JP | 9-218233 | 8/1997 |
| JP | 10-022851 | 1/1998 |
| JP | 11-064432 | 3/1999 |
| JP | 11-169338 | 6/1999 |
| JP | 2000-49718 | 2/2000 |
| JP | 2000-134121 | 5/2000 |
| JP | 2001-273467 | 10/2001 |
| JP | 2002-319907 | 10/2002 |
| JP | 2003-019111 | 1/2003 |
| JP | 2005-218703 | 8/2005 |
| JP | 2005-245596 | 9/2005 |
| JP | 2005-334540 | 12/2005 |
| WO | WO 2005/074785 | 8/2005 |

OTHER PUBLICATIONS

Office Action issued for corresponding Japanese Application No. 2005-306116 dated Jun. 7, 2011.

Decision of Grant issued by the Japanese Patent Office on May 17, 2011 in connection with corresponding Japanese Patent Application No. 2005-311663.

Partial English translation of Japanese Office Action issued in connection with Japanese Patent Application No. 2005-311663 on May 17, 2011.

PCT/ISA/210, "International Search Report", for PCT/JP2006/317007.

* cited by examiner

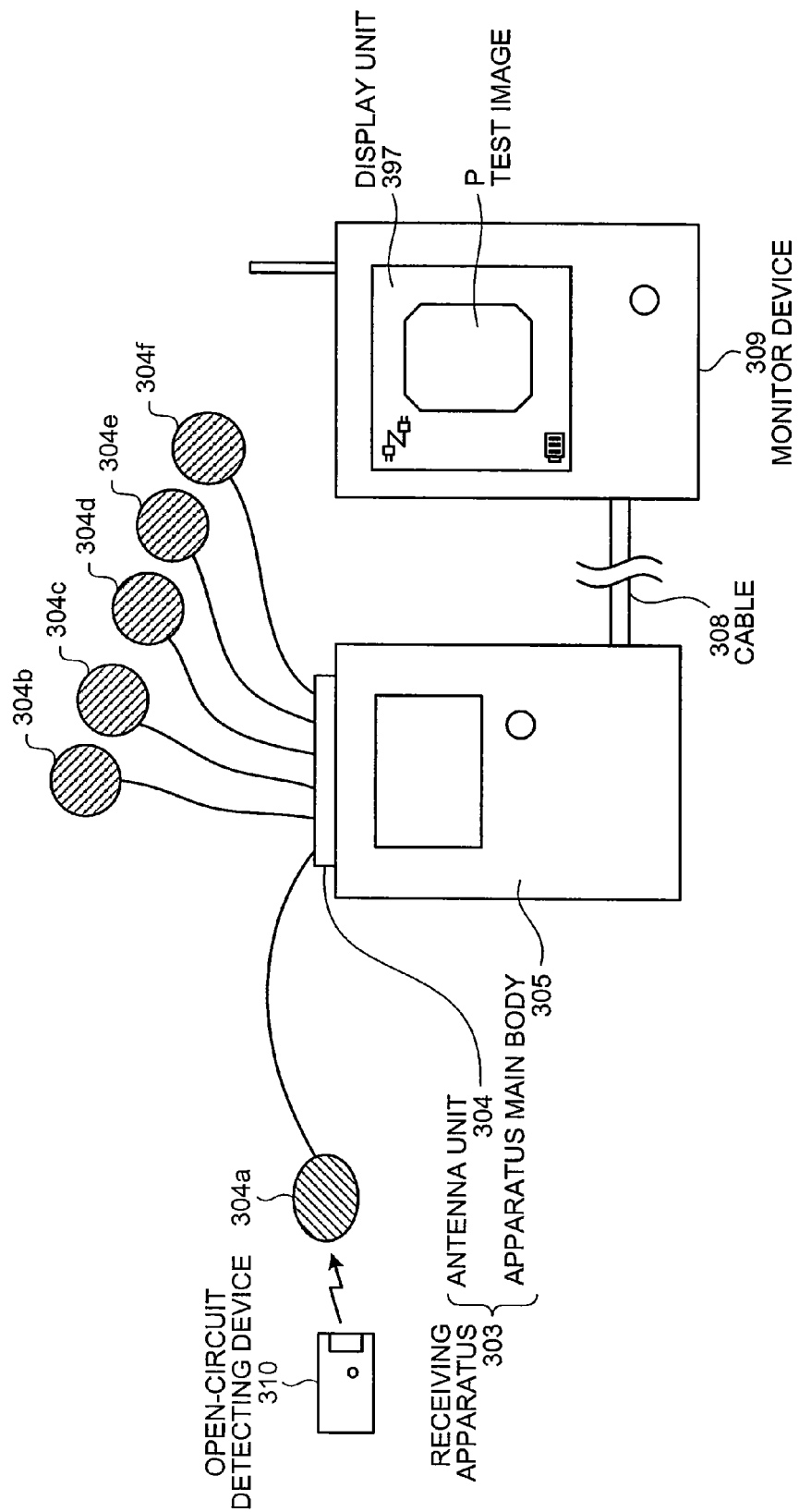

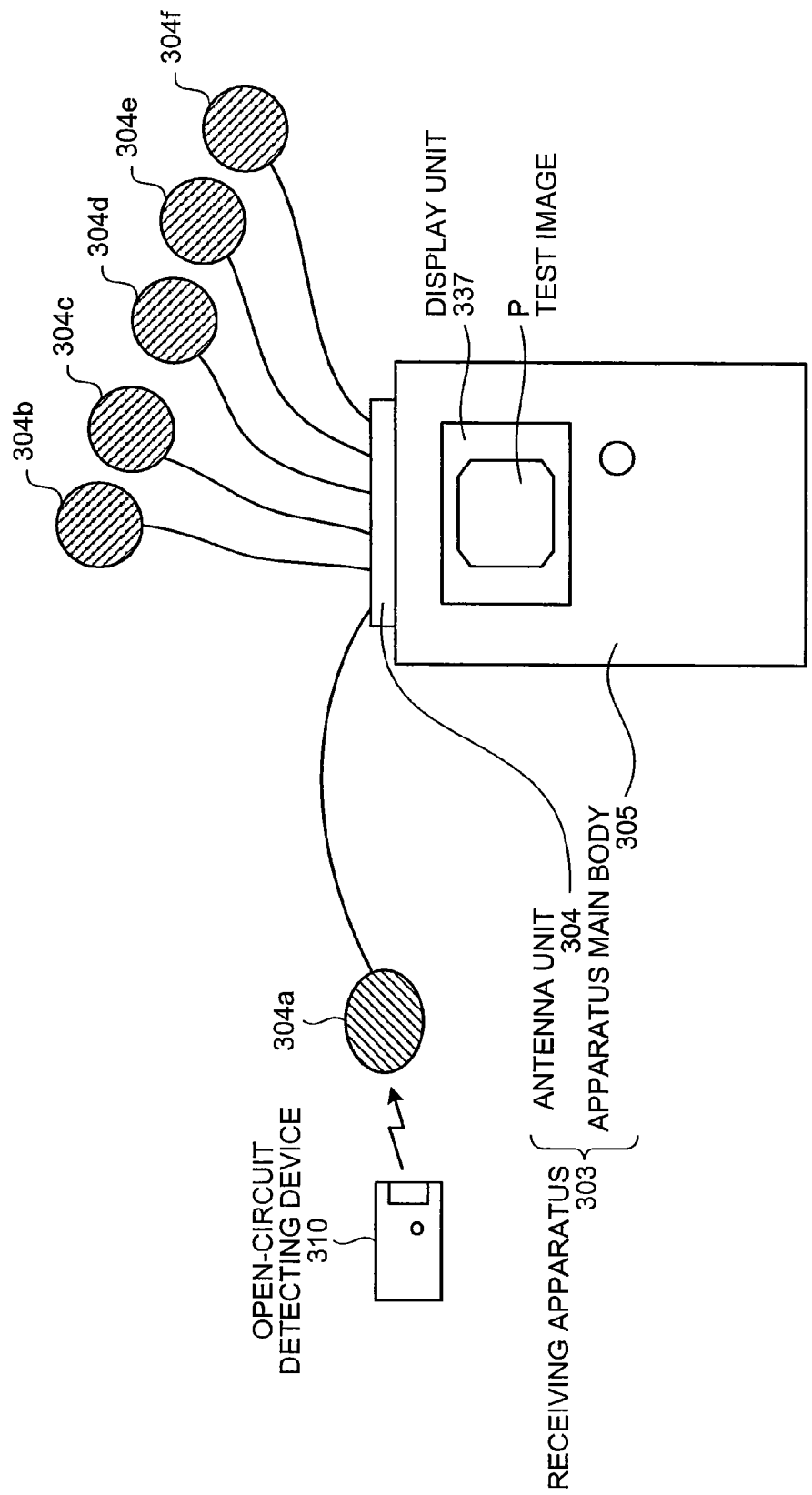

RECEIVING APPARATUS

CROSS REFERENCE TO RELATED APPLICATION

The present application is a 35 U.S.C. §§371 national phase conversion of PCT/JP2006/317007, filed 29 Aug. 2006, which claims priority of Japanese Patent Application No. 2005-262045 filed 9 Sep. 2005, and claims priority of Japanese Patent Application No. 2005-306116 filed 20 Oct. 2005 and claims priority of Japanese Patent Application No. 2005-311663 filed 26 Oct. 2005 which which is herein incorporated by reference.

TECHNICAL FIELD

The present invention relates to a receiving apparatus that selecting and switching one of a plurality of feeders connected to a plurality of receiving antennas, respectively using a selecting/switching unit, and that receives transmitted information from a mobile transmitting apparatus through the selected and switched feeder and the receiving antenna.

BACKGROUND ART

Recently, in the field of endoscopes, a swallowable capsule endoscope including an imaging function and a radio communication function has been proposed. Development of an in-vivo information acquiring system for acquiring image data on an intra-subject image picked up by the capsule endoscope is underway. In this in-vivo information acquiring system, the capsule endoscope moves in a subject's organ, e.g., the stomach or the small intestine, according to the peristaltic movement of the organ until natural discharge of the capsule endoscope after the subject, e.g., patient swallows the capsule endoscope from his/her mouth. Furthermore, the capsule endoscope functions to pick up intra-subject images at predetermined intervals, e.g., 0.5-second intervals.

During the movement of the capsule endoscope in the body of the subject, the image data obtained by the capsule endoscope is sequentially transmitted to the outside by radio communication, and received by a receiving apparatus through receiving antennas distributed outside of the subject. The receiving apparatus demodulates a radio signal received through the receiving antennas into an image signal, performs a predetermined image processing on the obtained image signal, and generates image data. Thereafter, the receiving apparatus sequentially stores image data thus generated (that is, information on images picked up by the capsule endoscope) in a storage medium. By causing the subject to carry such a receiving apparatus including the radio communication function and a memory function, the subject can move freely until the discharge of the capsule endoscope after the subject swallows the capsule endoscope. A user, e.g., a doctor or a nurse, loads the image data stored in the storage medium of the receiving apparatus into a workstation, and diagnoses the subject while displaying the intra-subject images on a display of the workstation (see, for example, Patent Document 1).

Generally, a plurality of receiving antennas of the receiving apparatus for receiving the radio signals transmitted from the capsule endoscope are arranged to be distributed outside of the subject's body. Furthermore, the receiving apparatus selects and switches to one receiving antenna with fewer radio-signal reception errors and receives the radio signals through the selected receiving antenna.

Patent Document 1: Japanese Patent Application Laid-Open No. 2003-19111

DISCLOSURE OF INVENTION

Problem to be Solved by the Invention

Meanwhile, the doctor or nurse needs to observe the intra-subject images picked up by the capsule endoscope as many as possible to accurately and closely diagnose the subject. Therefore, the receiving apparatus is desired to ensure receiving the radio signals from the capsule endoscope inserted into the subject and to acquire as much intra-subject image data included in the radio signals as possible. To this end, if a capsule endoscopy examination is carried out to obtain intra-subject images by inserting the capsule endoscope into the subject, it is verified whether the receiving apparatus is in a normal state in which the receiving apparatus can acquire the image data obtained by the capsule endoscope.

Specifically, the receiving antennas of the receiving apparatus are distributed to locations (a plurality of locations on a body surface) outside of the subject, and connected to one receiving apparatus main body through coaxial cables, respectively. The receiving antennas are repeatedly connected to the receiving apparatus through the respective coaxial cables and repeatedly attached to the subject whenever the capsule endoscopy examination is carried out. Due to this, if the number of capsule endoscopy examinations increases, an open-circuit tends to occur to each of the coaxial cables.

For this reason, before the capsule endoscopy examination, an open-circuit check is performed on the coaxial cables or the like that connect the respective receiving antennas to the receiving apparatus. In this case, the conventional receiving apparatus performs an open-circuit detection with respect to the receiving antennas to confirm whether the respective receiving antennas operate normally before the capsule endoscope is inserted into the subject.

This open-circuit detection with respect to the receiving antennas is carried out by using a dummy signal generator that generates the radio signals generated by the capsule endoscope as dummy signals. Furthermore, the dummy signal generator is made closer to each of the receiving antennas to check a reception state of each receiving antenna. It, therefore, takes disadvantageously long operation time for detecting whether an open-circuit occurs to each of the receiving antennas for the capsule endoscopy examination.

The present invention has been achieved in view of the above-stated respects. It is an object of the present invention to provide a receiving apparatus capable of ensuring detecting whether an open-circuit occurs to a feeder with simple configuration within short time.

Means for Solving Problem

A receiving apparatus according to the present invention for receiving transmitted information transmitted from a moving transmitting apparatus through a selected and switched feeder and a receiving antenna, the receiving apparatus includes a selecting/switching unit that selects and switches one of a plurality of feeders connected to a plurality of receiving antennas, respectively; a detective selecting/switching unit that branches the plurality of feeders near the selecting/switching unit, respectively, and selects and switches one of the branched feeders; a grounding unit, provided between each of the feeders and each of the receiving antennas, that grounds each of the feeders; an open-circuit detecting unit that applies a direct-current voltage to the feeder selected and switched by the detective selecting/switching unit through a constant-current source, and that detects whether an open-circuit occurs in the selected and switched feeder based on whether a voltage of the feeder is equal to a ground voltage; and a control unit that controls the detective selecting/switching unit to perform selection and switching, and makes the open-circuit detecting unit to detect an open-circuit synchronously with the control over the selection and switching of the detective selecting/switching unit.

In the receiving apparatus according to the present invention, each of the receiving antennas may be an open receiving antenna, each of the feeders and each of the receiving antennas may be connected to each other by a transformer balun, and a feeder-side of the transformer balun may be grounded.

In the receiving apparatus according to the present invention, each of the receiving antennas may be an open receiving antenna, each of the feeders and each of the receiving antennas may be connected to each other by a short-circuit element, and one end of the short-circuit element may be grounded.

In the receiving apparatus according to the present invention, each of the receiving antennas may be a loop antenna, and one end at which each of the feeders is connected to each of the receiving antennas may be grounded.

In the receiving apparatus according to the present invention, each of the feeders may be a coaxial cable, and an external conductor may be grounded.

In the receiving apparatus according to the present invention, the control unit may perform a control to display by outputting a result of the open-circuit detection.

Effect of the Invention

The receiving apparatus according to the present invention includes the detective selecting/switching unit that branches the plurality of feeders near the selecting/switching unit, respectively and that selects and switches one of the branched feeders, and the grounding unit provided between each of the feeders and each of the receiving antennas and grounding each of the feeders. Furthermore, the receiving apparatus according to the present invention includes the open-circuit detecting unit that applies a direct-current voltage to the feeder selected and switched by the detective selecting/switching unit through a constant-current source and that detects whether an open-circuit occurs to the selected feeder based on whether a voltage of the selected feeder is equal to a ground voltage. Moreover, the control unit controls the detective selecting/switching unit to perform selection and switching, and controls the open-circuit detecting unit to perform an open-circuit detection synchronously with the control over the selection and switching of the detective selecting/switching unit. Therefore, it is advantageously possible to ensure detecting whether an open-circuit occurs to each feeder with simple configuration within short time.

BRIEF DESCRIPTION OF DRAWINGS

FIG. 19 is a pattern diagram for explaining a method of detecting whether an open-circuit occurs to each of receiving antennas.

FIG. 20 is a pattern diagram for explaining a modification of the open-circuit detecting method according to the ninth embodiment of the present invention.

EXPLANATIONS OF LETTERS OR NUMERALS

Figure 1:
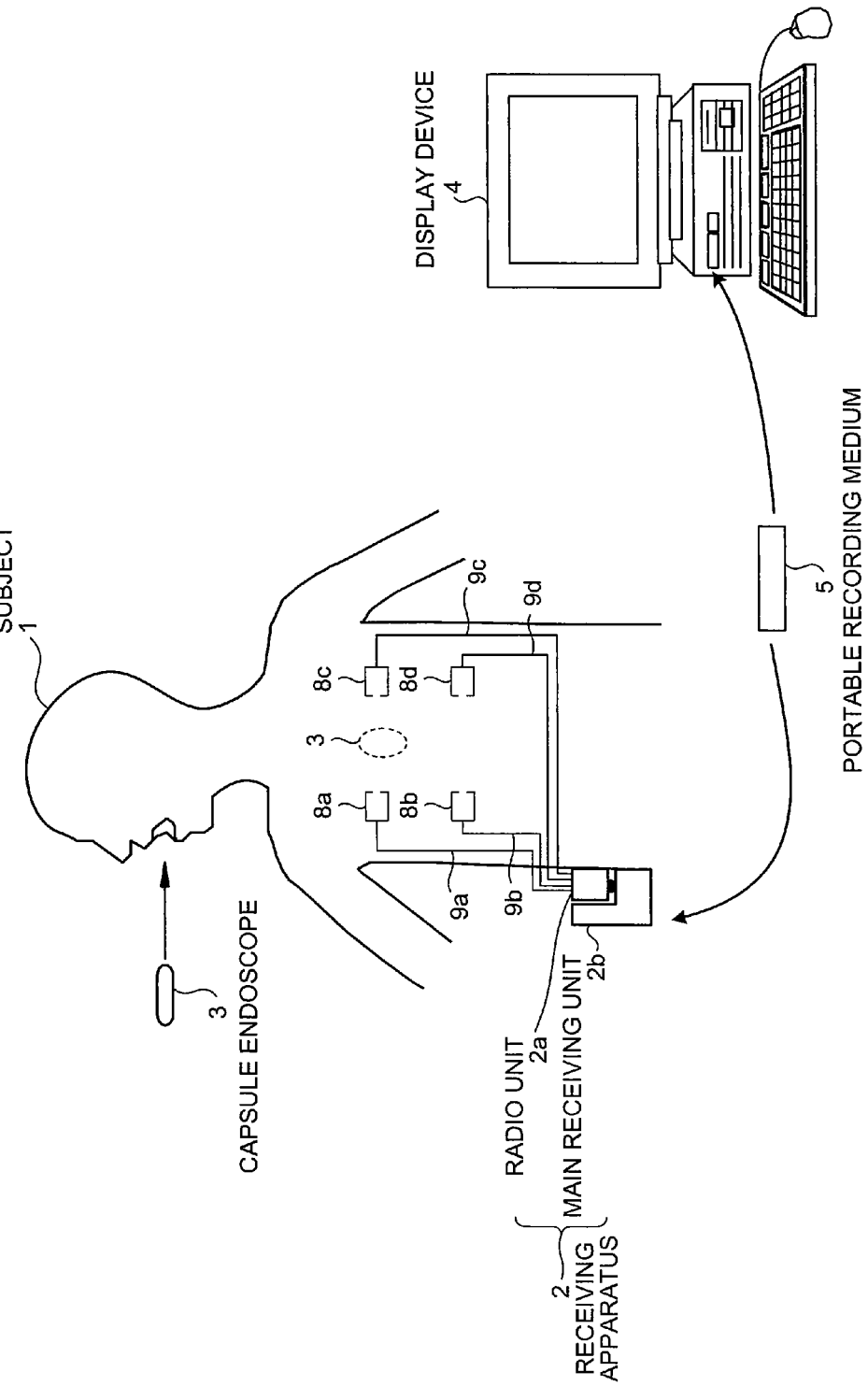
FIG. 1 is a block diagram showing a schematic configuration of a capsule endoscope system using a receiving apparatus according to a first embodiment of the present invention.

1 Subject
2, 102, 303 Receiving apparatus
2a, 102a Radio unit
2b, 102b Main receiving unit
3, 103, 302 Capsule endoscope
4, 104 Display device
5, 105, 307 Portable recording medium
8a-8d, 81a, 82a, 304a-304f, 390 Receiving antenna
9a-9d Coaxial cable
10 Transformer balun 10A Short-circuit element
20, 22 Changeover switch
21, 111, 332, 391 Receiving circuit
23 Open-circuit detecting circuit
24, 112, 334, 392 Signal processing circuit
25, 113 A/D converter
26, 318, 339, 398 Control unit
27, 114, 122, 337, 397 Display unit
28, 115, 124, 335 Storage unit
29, 116, 319, 340, 399 Power supply unit
90a, 91a, 92a Core wire
90A, 91A, 92A External conductor
121, 311, 336, 396 Input unit
123 Output unit
124a Statistical data
125 External communication interface
200 Direct-current source
201 Switch
202 Comparator
203 Constant-current source
260 Switching controller
304 Antenna unit
305 Apparatus main body
306 Workstation
308, 321 Cable
309 Monitor device
310 Open-circuit detecting device
312 Imaging unit
313 Image processor
314 Pattern image generator
315, 395 Switching circuit
316 Transmitting circuit
317 Transmitting antenna
322 Cradle
330 Connector
331 Antenna switching unit
333 Switching control circuit
338, 394 Communication I/F
339a Operation check unit
393 Connection detector
A1-An Receiving antenna
C1, C2 Control unit
C1a Switching controller
C2an Open-circuit detecting processor
P Test image

BEST MODE(S) FOR CARRYING OUT THE INVENTION

Exemplary embodiments of the present invention will be described hereinafter with reference to the accompanying drawings.

First Embodiment

FIG. 1 is a block diagram showing a schematic configuration of a capsule endoscope system using a receiving apparatus 2 according to a first embodiment of the present invention. As shown in FIG. 1, when being inserted into a subject 1, a capsule endoscope 3 picks up an in-vivo image of the subject 1 while moving in the body of the subject 1, and transmits an image signal corresponding to the image thus picked up to the outside of the subject 1 as a radio signal.

The receiving apparatus 2 includes a plurality of receiving antennas 8a to 8d distributed to outside the body of the subject 1, coaxial cables 9a to 9d connected to the respective receiving antennas 8a to 8d, a radio unit 2a connected to the coaxial cables 9a to 9d, and a main receiving unit 2b connected to the radio unit 2a.

The image signal transmitted from the capsule endoscope 3 is received by the receiving antennas 8a to 8d, and loaded into the main receiving unit 2b through the radio unit 2a. The main receiving unit 2b selects one receiving antenna having the highest received electric-field strength from among the receiving antennas 8a to 8d to receive image signals, sequentially receives the image signals received by this selected receiving antenna, and stores a set of images before the capsule endoscope 3 is discharged from the body of the subject 1.

After discharge of the capsule endoscope 3 from the body of the subject 1, a portable recording medium 5 is detached from the main receiving unit 2b and attached to a display device 4. The display device 4 reads the set of images stored in the portable recording medium 5 and performs a display processing or the like on the images.

It is to be noted that the capsule endoscope system that includes the capsule endoscope and the display device as shown in FIG. 1 is a system in which the receiving apparatus receives (acquires) in-vivo images picked up by the capsule endoscope through the receiving antennas, and in which the display device displays the acquired in-vivo images. The capsule endoscope system is often referred to as "radio in-vivo information acquiring system" or simply "in-vivo information acquiring system".

Figure 2:
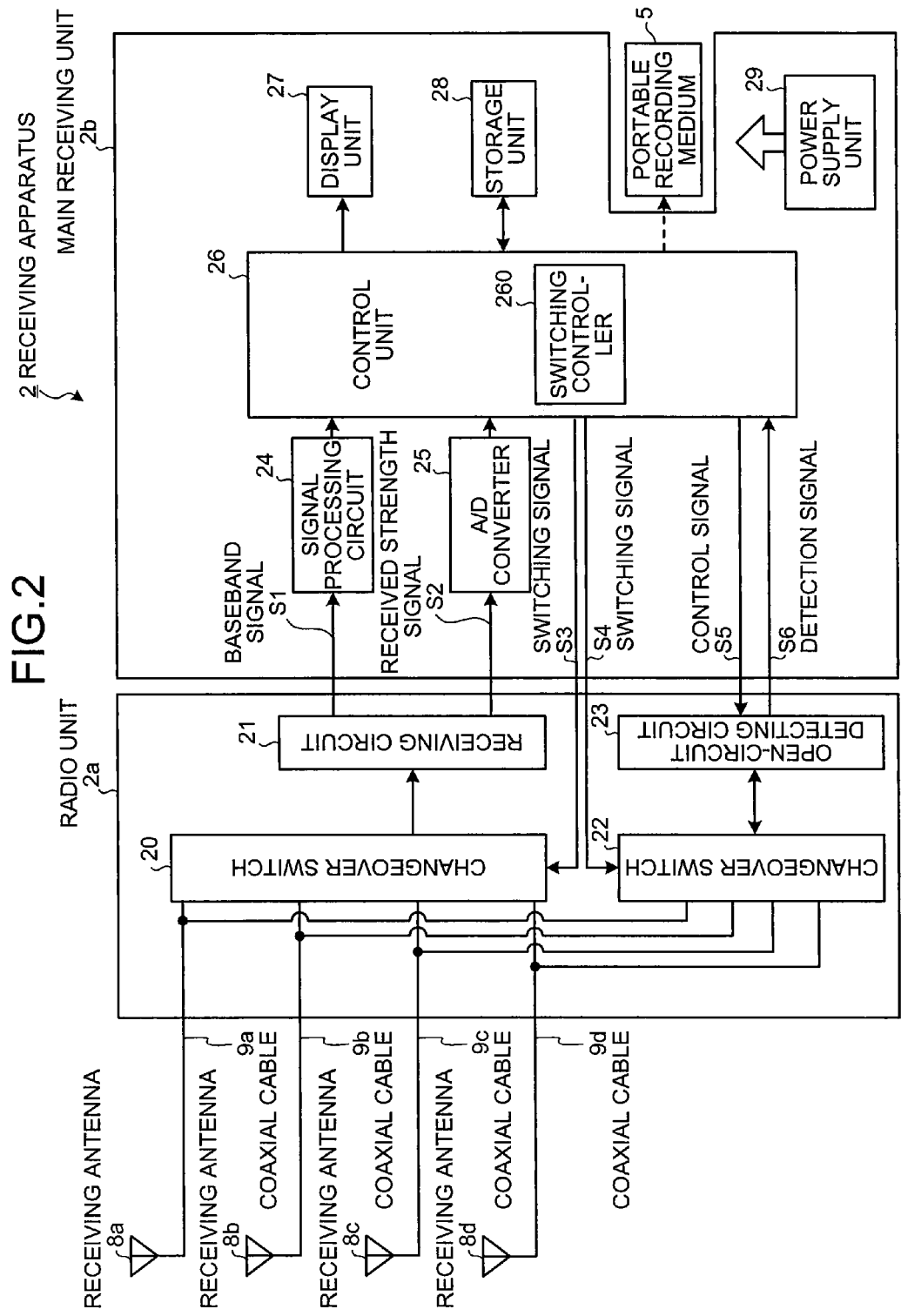
FIG. 2 is a block diagram showing a schematic configuration of the receiving apparatus according to the first embodiment of the present invention.

FIG. 2 is a block diagram showing a configuration of the receiving apparatus 2. As shown in FIG. 2, the radio unit 2a includes changeover switches 20 and 22 each connected to the receiving antennas 8a to 8d, a receiving circuit 21 that receives a received signal from the changeover switch 20, and an open-circuit detecting circuit 23 connected to the changeover switch 22.

When a switching signal S3 is input to the changeover switch 20, the changeover switch 20 selects one coaxial cable instructed by the switching signal S3 from among the coaxial cables 9a to 9d. The receiving circuit 21 receives an image signal through the coaxial cable selected by the changeover switch 20, and outputs a baseband signal S1 including this image signal and a received strength signal S2 indicating a received electric-field strength of the image signal to the main receiving unit 2b.

When a switching signal S4 for instructing changeover among the coaxial cables similarly to the switching signal S3 is input to the changeover switch 22, the changeover switch 22 selects one coaxial cable instructed by this switching signal S4 from among the coaxial cables 9a to 9d, and connects this selected coaxial cable to the open-circuit detecting circuit 23. When a control signal S5 for instructing an open-circuit detection is input to the open-circuit detecting circuit 23, the open-circuit detecting circuit 23 performs an open-circuit check on the selected, connected coaxial cable. Furthermore, the open-circuit detecting circuit 23 outputs a result of this open-circuit check to the main receiving unit 2b as a detection signal S6.

The main receiving unit 2b includes a signal processing circuit 24, an A/D converter 25, a control unit 26 including a switching controller 260, a display unit 27, a storage unit 28, a detachable portable recording medium 5, and a power supply unit 29. The power supply unit 29 supplies power to the above-stated constituent elements, respectively.

The signal processing circuit 24 generates an image signal from the baseband signal S1 input from the receiving circuit 21, and outputs the image signal to the control unit 26. The A/D converter 25 performs A/D conversion to convert the received strength signal S2 input from the receiving circuit 21 into a digital signal indicating the received electric-field strength, and outputs the digital signal to the control unit 26.

The control unit 26 records the image signal input from the signal processing circuit 24 in the portable recording medium 5, and exercises a processing control to display and output an image on and to the display unit 27 if it is necessary to do so. Furthermore, the switching controller 260 selects one receiving antenna having the highest received electric-field strength based on the digital signal input from the A/D converter 25 and indicating the received electric-field strength. The switching controller 260 then outputs the switching signal S3 for instructing switching to the coaxial cable connected to this receiving antenna to the changeover switch 20. Moreover, the switching controller 260 outputs the switching signal S4 for instructing switching among the coaxial cables for the open-circuit check to the changeover switch 22. The switching controller 260 also outputs the control signal S5 for instructing the open-circuit check to correspond to this switching signal S4, to the open-circuit detecting circuit 23, and receives the detection signal S6.

Figure 3:
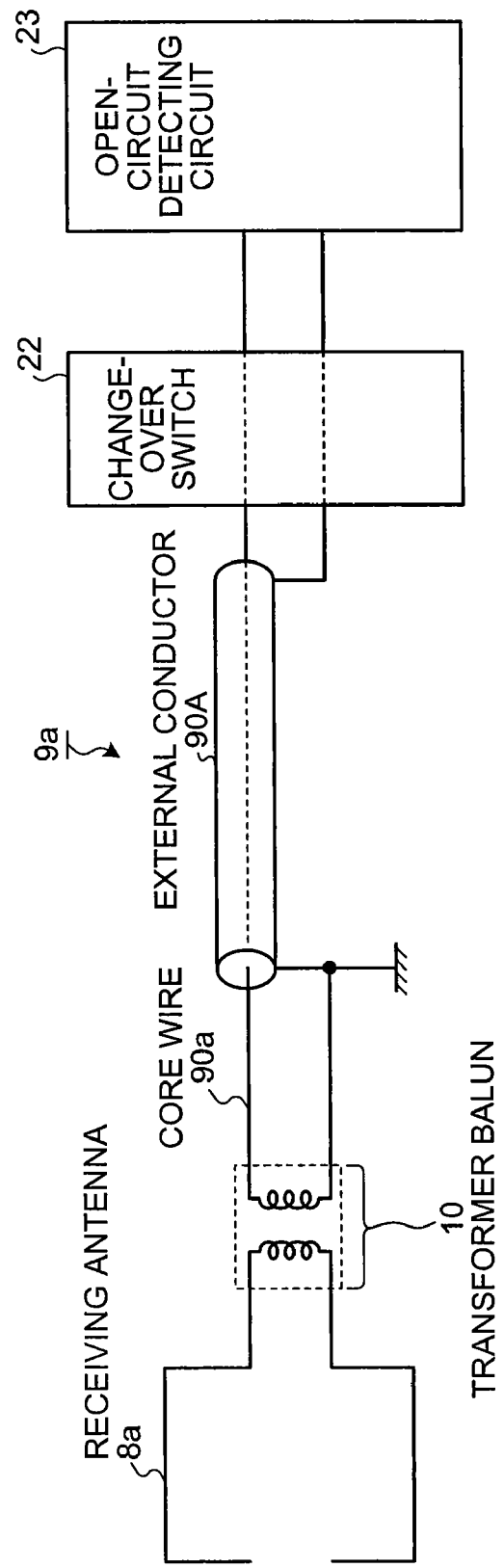
FIG. 3 is a schematic view showing the connection relation between a coaxial cable and a receiving antenna according to the first embodiment of the present invention.

FIG. 3 is a block diagram showing the specific connection relation between the receiving antenna 8*a* and the coaxial cable 9*a*. As shown in FIG. 3, the receiving antenna 8*a* is an open antenna, and the coaxial cable 9*a* includes a core wire 90*a*, which is an internal conductor, and an external conductor 90A.

The receiving antenna 8*a* is connected to the coaxial cable 9*a* by a transformer balun 10. Coils are formed on a coaxial cable 9*a*-side of the receiving antenna 8*a* and a receiving antenna 8*a*-side of the coaxial cable 9*a*, respectively. The receiving antenna 8*a* is electromagnetically coupled to the coaxial cable 9*a*, thus reducing a leakage current generated by the connection between the receiving antenna 8*a* that is a balanced line and the coaxial cable 9*a* that is an unbalanced line. The coil on the coaxial cable 9*a*-side is formed on a tip end of the core wire 90*a*, and the coil and the external conductor 90A are grounded.

Figure 4:
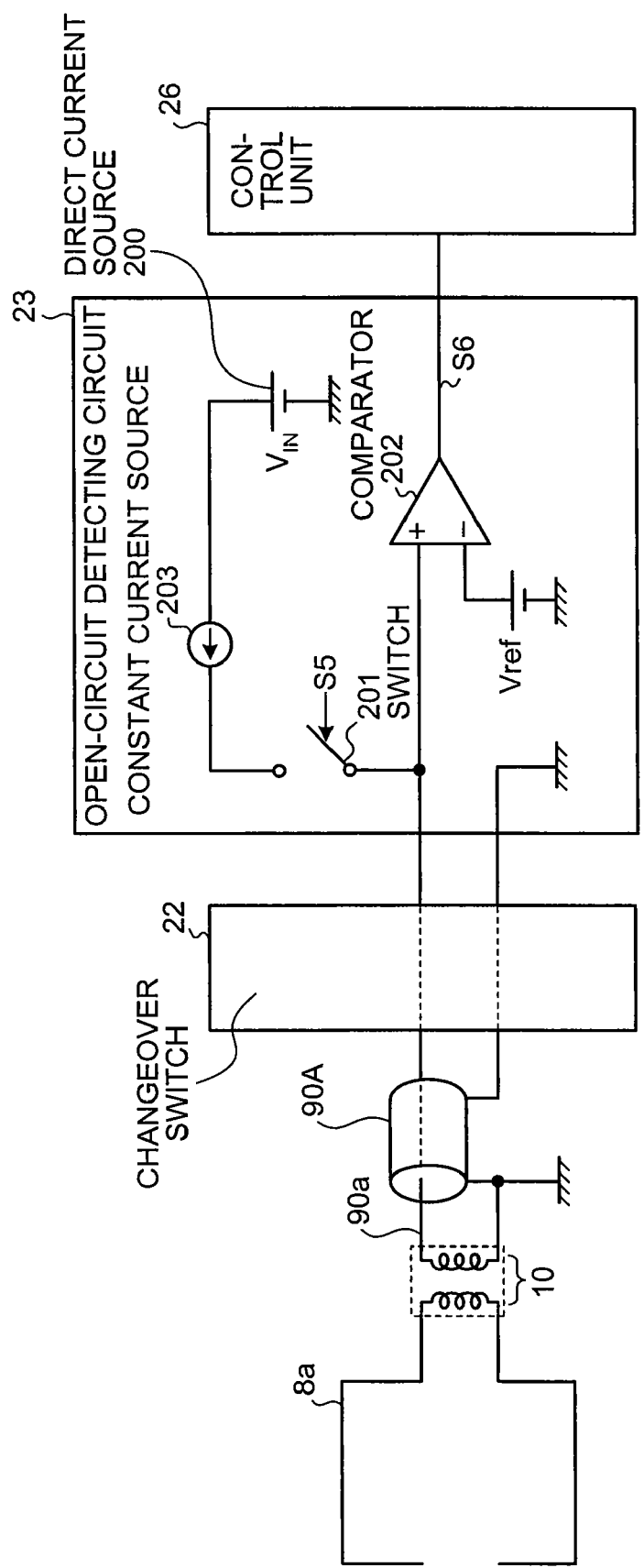
FIG. 4 is a block diagram showing a schematic configuration ranging from an open-circuit detecting circuit to the receiving antenna if no open-circuit occurs to the coaxial cable.

FIG. 4 is a block diagram mainly showing a configuration of the open-circuit detecting circuit 23. As shown in FIG. 4, this open-circuit detecting circuit 23 includes a comparator 202 that compares an input voltage with a threshold voltage Vref and that outputs a result of the comparison as the detection signal S6. The threshold voltage Vref is input to one input terminal of the comparator 202, and the core wire 90*a* is connected to the other input terminal of the comparator 202. A direct-current source 200 from which a direct current voltage $V_{IN}$ is output is connected to the core wire 90*a* through a switch 201 and a constant-current source 203. The switch 201 is turned on or off in response to the control signal S5. The voltage $V_{IN}$ is equal to or higher than the threshold voltage Vref. Alternatively, a resistor can be used in place of the constant-current source 203.

If no open-circuit occurs to the core wire 90*a* of the coaxial cable 9*a*, then the switch 201 is "closed", the voltage $V_{IN}$ is applied to the core wire 90*a*, and the core wire 90*a* is grounded through the transformer balun 10. Therefore, a voltage between the core wire 90*a* and the ground is equal to a ground voltage, and the voltage input to the other input terminal of the comparator 202 is equal to or lower than the threshold voltage Vref. As a result, the comparator 202 outputs the detection signal S6 indicating that the voltage input from the other input terminal is equal to or lower than the threshold voltage Vref. Moreover, the control unit 26 determines that no open-circuit occurs to the core wire 90*a*.

Figure 5:
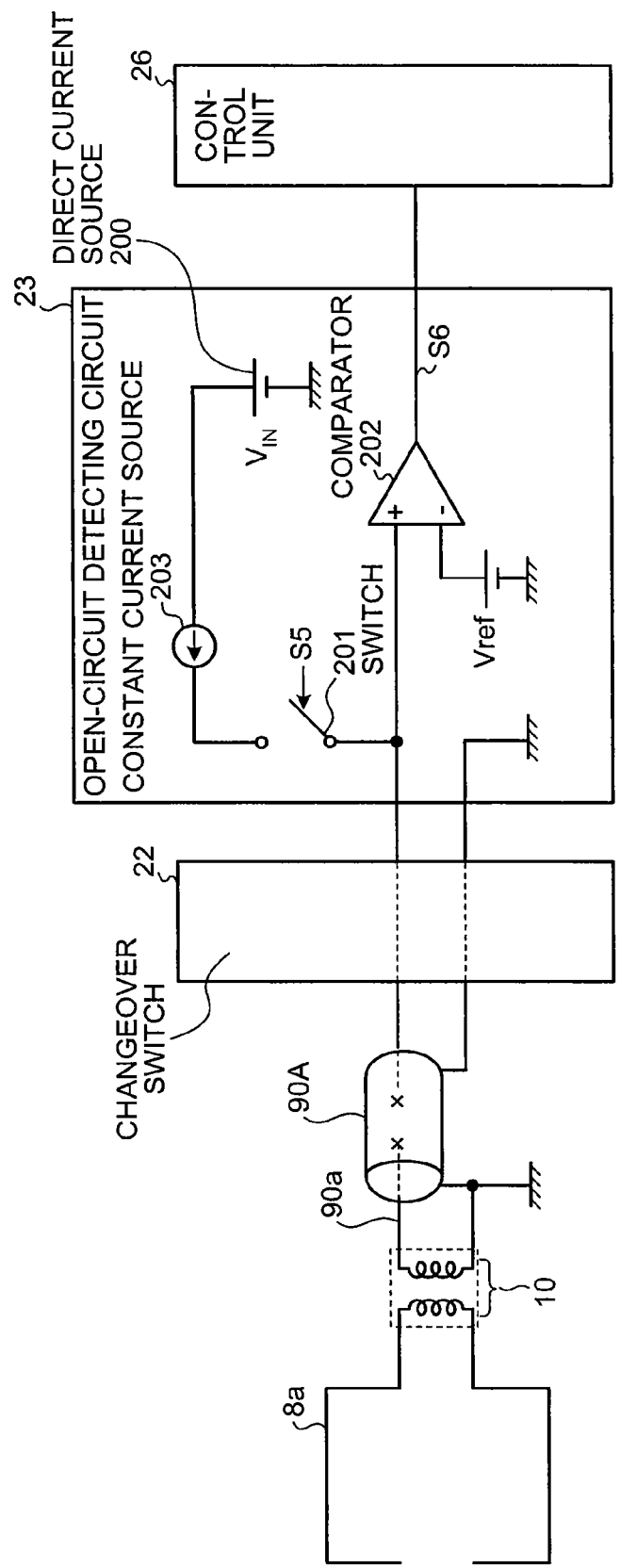
FIG. 5 is a block diagram showing a schematic configuration ranging from the open-circuit detecting circuit to the receiving antenna if an open-circuit occurs to the coaxial cable.

On the other hand, if an open-circuit occurs to the core wire 90*a* of the coaxial cable 9*a*, then the switch 201 is "closed", the voltage $V_{IN}$ is applied to the core wire 90*a* through the constant-current source 203, and the core wire 90*a* is not directly grounded as shown in FIG. 5. Therefore, the voltage $V_{IN}$ is applied to the other input terminal of the comparator 202 as it is. The comparator 202 outputs the detection signal S6 indicating that the voltage (voltage $V_{IN}$) input from the other input terminal is equal to or higher than the threshold voltage Vref. Moreover, the control unit 26 determines that an open-circuit occurs to the core wire 90*a*.

The control unit 26 outputs the switching signal S4 to select the next coaxial cable 9*b*, and performs an open-circuit check on this selected, next coaxial cable 9*b* using the open-circuit detecting circuit 23. The control unit 26 performs open-circuit checks on all the coaxial cables 9*a* to 9*d* in the same manner. The control unit 26 can thereby instantly determine whether an open-circuit occurs to each of the coaxial cables 9*a* to 9*d* and identify the coaxial cable to which an open-circuit occurs.

If the coaxial cable to which the open-circuit occurs is detected, the control unit 26 can assign a number or the like to the coaxial cable in advance so as to display the number of the coaxial cable to which the open-circuit occurs on the display unit 27. If it is detected that no open-circuit occurs to the coaxial cable, the fact that no open-circuit occurs can be displayed on the display unit 27.

If the image signal is being received, then the switching signals S3 and S4 can be set to the same signal, and the switching controller 260 of the control unit 26 can perform the open-circuit detection with respect to the switched coaxial cable. Alternatively, the coaxial cables for which the switching signals S3 and S4 are output to instruct the switching can be made different from each other, and the switching controller 260 can perform the open-circuit detection with respect to the coaxial cables through which no image signal is received. As another alternative, switching by the changeover switches 20 and 22 can be temporally separated from each other and the open-circuit detection can be performed while no receiving processing is performed. As yet another alternative, the open-circuit detection can be performed if the receiving apparatus 2 does not perform the receiving processing, for example, before examination or after examination. As still another alternative, if it is detected that an open-circuit occurs to a coaxial cable, the control unit 26 can exercise a control not to switch to the receiving antenna connected to this coaxial cable to which the open-circuit occurs.

In this first embodiment, the coaxial cables 9*a* to 9*d* are branched and the direct-current voltage is applied to each branched coaxial cable. It is thereby possible to easily detect whether an open-circuit occurs to each coaxial cable and to promptly identify the coaxial cable to which an open-circuit occurs.

This first embodiment has been described while showing the four coaxial cables 9*a* to 9*d*. However, the number of coaxial cables is not limited to four. Moreover, if a connection failure occurs to a coaxial cable, the result of the open-circuit check differs whenever an open-circuit check is carried out. The control unit 26 can store the result of the open-circuit check on each coaxial cable in the storage unit 28 so as to be able to deal with this connection failure. If occurrence of a predetermined number of open-circuits is detected, the control unit 26 can cause a warning for urging replacement to be displayed on the display unit 27.

Second Embodiment

A second embodiment of the present invention will be described. In the first embodiment, the core wire 90*a* of the coaxial cable 9*a* is grounded using the transformer balun 10 to perform the open-circuit detection on the coaxial cable 9a. In this second embodiment, the core wire of the coaxial cable is grounded using a short-circuit element realized by a diode or the like to perform the open-circuit detection with respect to the coaxial cable.

Figure 6:
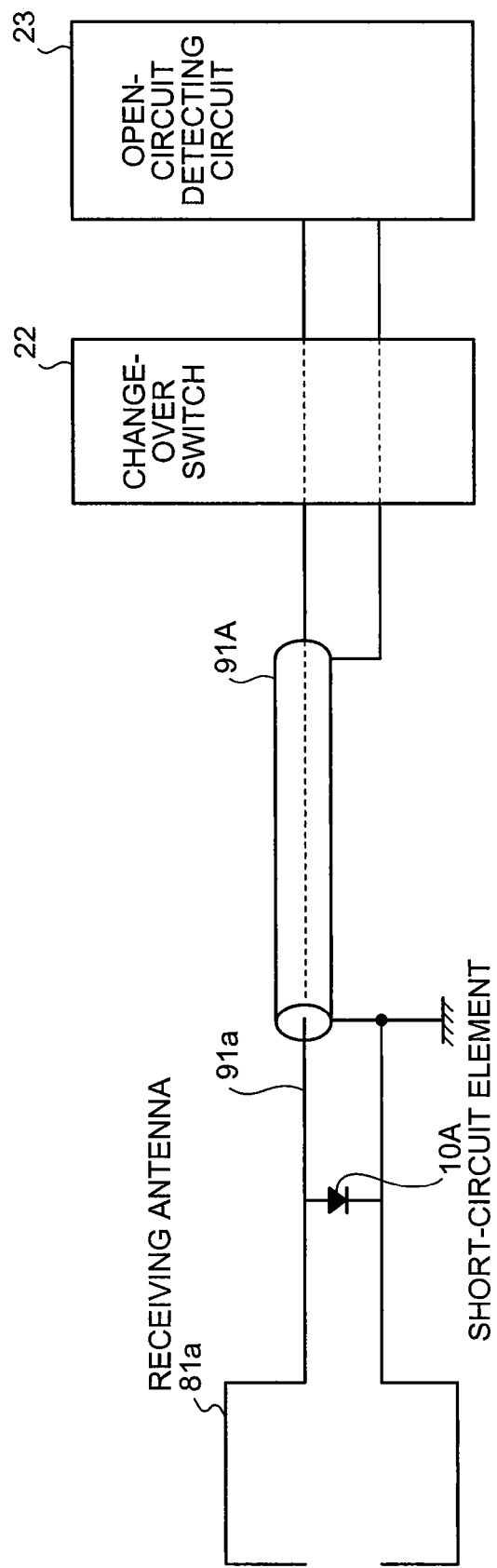
FIG. 6 is a schematic view showing the connection relation between a coaxial cable and a receiving antenna according to a second embodiment of the present invention.

FIG. 6 is a schematic view showing the connection relation between a receiving antenna 81a corresponding to the receiving antenna 8a shown in FIG. 5 and a coaxial cable 91a corresponding to the coaxial cable 90A shown in FIG. 5. As shown in FIG. 6, one end of the open receiving antenna 81a is connected to the core wire 91a and the other end thereof is connected to a grounded external conductor 91A. The other constituent elements are the same as those according to the first embodiment, and the same constituent elements are denoted by the same reference symbols as those according to the first embodiment, respectively.

In a connection part between the receiving antenna 81a and the coaxial cable 91A, the core wire 91a is connected to the external conductor 91A by a short-circuit element 10A, the short-circuit element 10A allows direct-current-like continuation of the core wire 91a to the external conductor 91A to ground the core wire 91a.

If no open-circuit occurs to the core wire 91a of the coaxial cable 9a, then the switch 201 is "closed", the voltage $V_{IN}$ is applied to the core wire 91a through the constant-current source 203, and the core wire 91a is grounded through the short-circuit element 10A. Therefore, a voltage between the core wire 91a and the ground is equal to the ground voltage, and the voltage input to the other input terminal of the comparator 202 is equal to or lower than the threshold voltage Vref. As a result, the comparator 202 outputs the detection signal S6 indicating that the voltage input from the other input terminal is equal to or lower than the threshold voltage Vref. Moreover, the control unit 26 determines that no open-circuit occurs to the core wire 91a.

On the other hand, if an open-circuit occurs to the core wire 91a of the coaxial cable 9a, then the switch 201 is "closed", the voltage $V_{IN}$ is applied to the core wire 91a through the constant-current source 203, and the core wire 91a is not directly grounded. Therefore, this voltage $V_{IN}$ is applied to the other input terminal of the comparator 202 as it is. The comparator 202 outputs the detection signal S6 indicating that the voltage (voltage $V_{IN}$) input from the other input terminal is equal to or higher than the threshold voltage Vref. Moreover, the control unit 26 determines that an open-circuit occurs to the core wire 91a.

The control unit 26 outputs the switching signal S4 to select the next coaxial cable 9b, and performs an open-circuit check on this selected, next coaxial cable 9b using the open-circuit detecting circuit 23. The control unit 26 performs open-circuit checks on all the coaxial cables 9a to 9d in the same manner. The control unit 26 can thereby instantly determine whether an open-circuit occurs to each of the coaxial cables 9a to 9d and identify the coaxial cable to which an open-circuit occurs.

Third Embodiment

A third embodiment of the present invention will be described. In the first and second embodiments, the receiving antennas 8a and 81a are both open antennas, and the core wires 90a and 91a are grounded through the transformer balun 10 and the short-circuit element 10A, respectively. In this third embodiment, each receiving antenna is a loop antenna, and the core wire is grounded through this loop receiving antenna.

Figure 7:
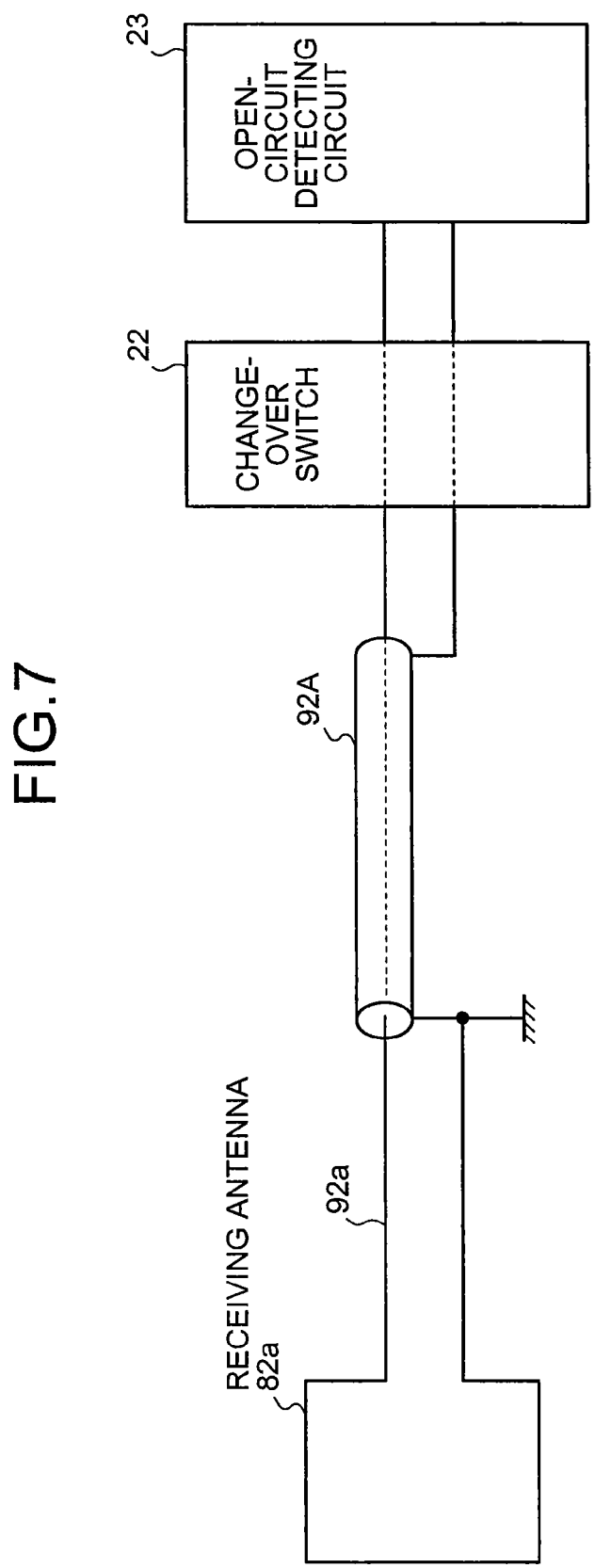
FIG. 7 is a schematic view showing the connection relation between a coaxial cable and a receiving antenna according to a third embodiment of the present invention.

FIG. 7 is a schematic view showing the connection relation between a receiving antenna 82a and a coaxial cable 92a. As shown in FIG. 7, one end of the loop receiving antenna 82a is connected to the core wire 92a of the coaxial cable 9a and the other end thereof is connected to a grounded external conductor 92A. The other constituent elements are the same as those according to the first and second embodiments, and the same constituent elements are denoted by the same reference symbols as those according to the first and second embodiment, respectively.

If no open-circuit occurs to the core wire 92a of the coaxial cable 9a, then the switch 201 is "closed", the voltage $V_{IN}$ is applied to the core wire 92a through the constant-current source 203, and the core wire 92a is grounded through the loop receiving antenna 82a. Therefore, a voltage between the core wire 91a and the ground is equal to the ground voltage, and the voltage input to the other input terminal of the comparator 202 is equal to or lower than the threshold voltage Vref. As a result, the comparator 202 outputs the detection signal S6 indicating that the voltage input from the other input terminal is equal to or lower than the threshold voltage Vref. Moreover, the control unit 26 determines that no open-circuit occurs to the core wire 92a.

On the other hand, if an open-circuit occurs to the core wire 92a of the coaxial cable 9a, then the switch 201 is "closed", the voltage $V_{IN}$ is applied to the core wire 91a through the constant-current source 203, and the core wire 92a is not directly grounded. Therefore, this voltage $V_{IN}$ is applied to the other input terminal of the comparator 202 as it is. The comparator 202 outputs the detection signal S6 indicating that the voltage (voltage $V_{IN}$) input from the other input terminal is equal to or higher than the threshold voltage Vref. Moreover, the control unit 26 determines that an open-circuit occurs to the core wire 92a.

The control unit 26 outputs the switching signal S4 to select the next coaxial cable 9b, and performs an open-circuit check on this selected, next coaxial cable 9b using the open-circuit detecting circuit 23. The control unit 26 controls the open-circuit detecting circuit 23 to perform open-circuit checks on all the coaxial cables 9a to 9d in the same manner. The control unit 26 can thereby instantly determine whether an open-circuit occurs to each of the coaxial cables 9a to 9d and identify the coaxial cable to which an open-circuit occurs.

Fourth Embodiment

A radio in-vivo information acquiring system that is the best mode for carrying out the invention will next be described.

The radio in-vivo information acquiring system including a receiving apparatus according to a fourth embodiment will first be described. This radio in-vivo information acquiring system employs a capsule endoscope as an example of a body-insertable apparatus.

Figure 8:
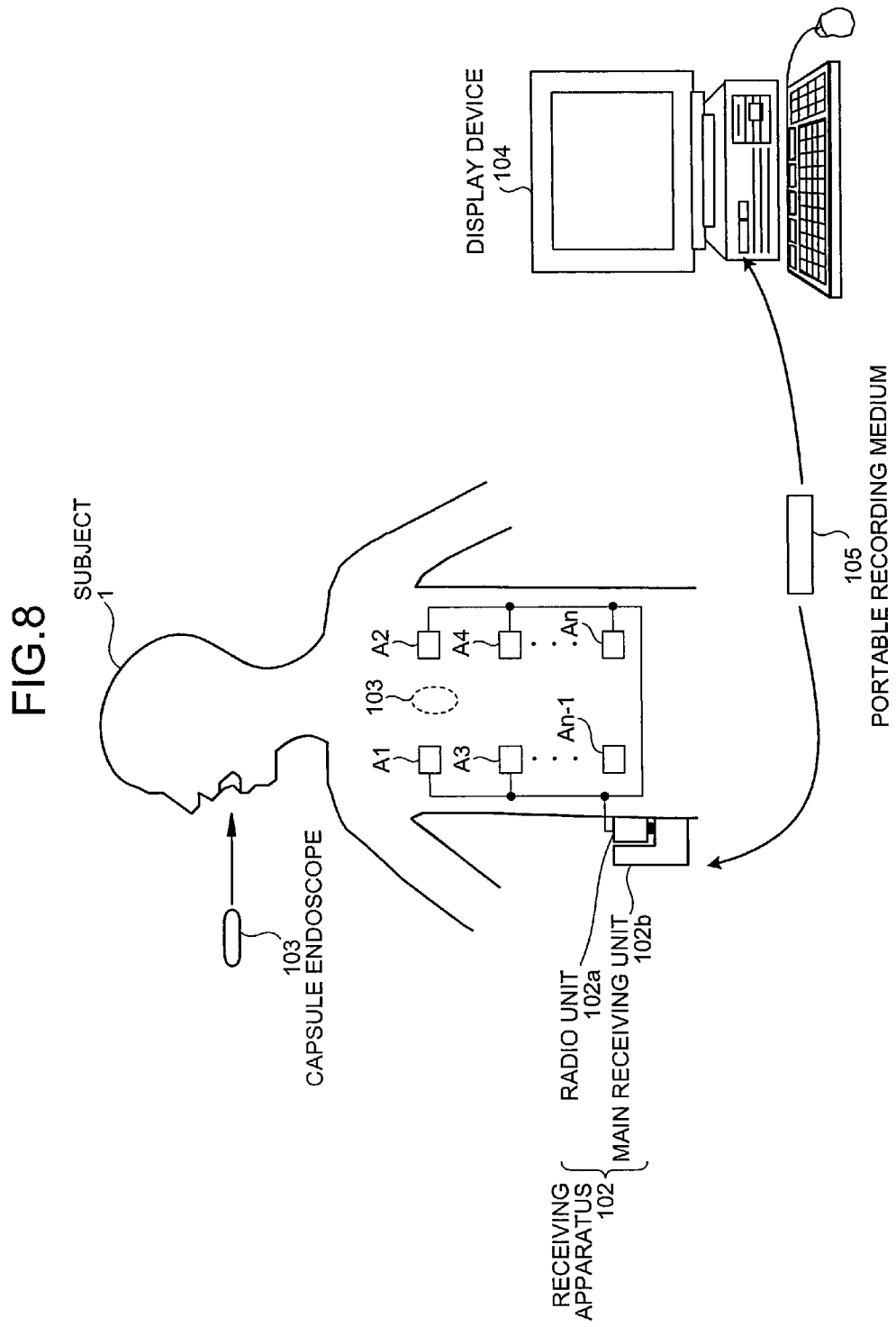
FIG. 8 is a pattern diagram showing an overall configuration of a radio in-vivo information acquiring system according to a fourth embodiment of the present invention.

FIG. 8 is a pattern diagram showing an overall configuration of the radio in-vivo information acquiring system. As shown in FIG. 8, the radio in-vivo information acquiring system includes a receiving apparatus 102 that includes a radio receiving function and a capsule endoscope (body-insertable apparatus) 103 that is inserted into the body of the subject 1, that picks up a body-cavity image as in-vivo information, and that transmits data such as an image signal to the receiving apparatus 102. The radio in-vivo information acquiring system also includes a display device 104 that displays the body-cavity image based on the image signal received by the receiving apparatus 102 and a portable recording medium 105 for transmitting and receiving data between the receiving apparatus 102 and the display apparatus 104. The receiving apparatus 102 includes a radio unit 102a including a plurality of receiving antennas A1 to An attached to the body surface of the subject 1 and a main receiving unit 102b that performs a processing or the like on a radio signal received through the receiving antennas A1 to An. These units are detachably connected to each other through a connector or the like. Each of the receiving antennas A1 to An is provided in a jacket which the subject 1 can wear, and the receiving antennas A1 to An can be attached to the subject 1 by causing the subject 1 to wear this jacket. In this case, the receiving antennas A1 to An can be detachably provided in the jacket.

The display device 104, which displays the body-cavity image picked up by the capsule endoscope 103, is configured like a workstation or the like for displaying images based on the data obtained by the portable recording medium 105. Specifically, the display device 104 can be configured to directly display images by a CRT display, a liquid crystal display or the like or to output images to the other medium.

A Compact Flash (registered trademark) memory or the like is used as the portable recording medium 105. The portable recording medium 105 is detachable from the main receiving unit 102b and the display device 104, and functions to be able to output or record information when being attached to the main receiving unit 102b or the display device 104. Specifically, the portable recording medium 105 is attached to the main receiving unit 102b while the capsule endoscope 103 is moving in the body cavity of the subject 1, and the data transmitted from the capsule endoscope 103 is recorded in the portable recording medium 105. After the capsule endoscope 103 is discharged from the subject 1, that is, after the interior of the subject 1 is imaged, the portable recording medium 105 is detached from the main receiving unit 102b and attached to the display device 104. The display device 104 reads the recorded data. By allowing the portable recording medium 105 such as the compact flash (registered trademark) memory to transmit and receive data between the main receiving unit 102b and the display device 104, the subject 1 can move freely while the body cavity is being imaged, as compared with the main receiving unit 102b is connected to the display device 104 by wired connection. Furthermore, the portable recording medium 105 also contributes to reduction in time for transmitting and receiving the data between the main receiving unit 102b and the display device 104. While the portable recording medium 105 is employed to transmit and receive data between the main receiving unit 102b and the display device 104, such a medium is not limited to the portable recording medium 105. Alternatively, the other recording device can be used to be included in the main receiving unit 102b and connected to the display device 104 by wired or wireless connection so as to transmit and receive data therebetween.

Figure 9:
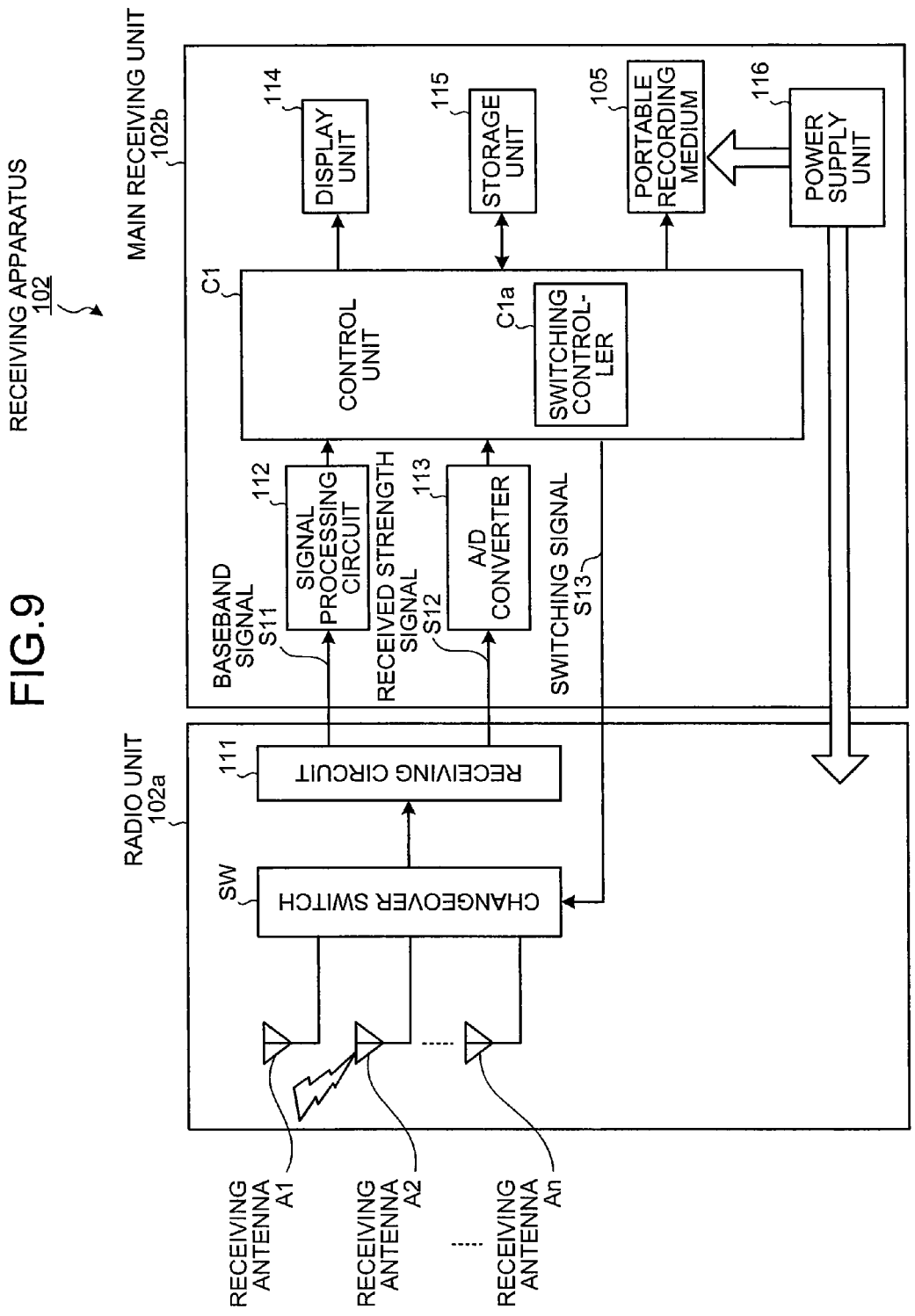
FIG. 9 is a block diagram showing a configuration of a receiving apparatus shown in FIG. 8.

Referring now to FIG. 9, the radio unit 102a and the main receiving unit 102b that constitute the receiving apparatus 102 will be described. FIG. 9 is a block diagram showing a configuration of the receiving apparatus 102. The radio unit 102a receives a radio signal transmitted from the capsule endoscope 103 and demodulates the radio signal into a baseband signal. As shown in FIG. 9, the radio unit 102a includes a changeover switch SW performing a connection switching processing for selecting and switching to one of the receiving antennas A1 to An, and a receiving circuit 111 connected in rear of this changeover switch SW and amplifying and demodulating the radio signal from one of the receiving antennas A1 to An selected and switched by and connected to the changeover switch SW.

The main receiving unit 102b receives and processes the baseband signal demodulated by the radio unit 102a. As shown in FIG. 9, the main receiving unit 102b includes a signal processing circuit 112 and an A/D converter 113 connected in rear of a receiving circuit 111, a display unit 114 that displays image data processed by the signal processing circuit 112 and information for various input processings, a storage unit 115 storing therein various information, a portable information recording medium 5, a control unit C1 that controls these constituent elements, and a power supply unit 116 that supplies power to the main receiving unit 102b and the radio unit 102a. The control unit C1 includes a switching controller C1a that controls antenna switching.

The receiving circuit 111 amplifies a high-frequency signal output from the changeover switch SW, outputs a demodulated baseband signal S11 to the signal processing circuit 112, and outputs a received strength signal S12 indicating a signal strength of the amplified high-frequency signal to the A/D converter 113. The image data processed by the signal processing circuit 112 is recorded in the portable recording medium 105 by the control unit C1, and an image is displayed on the display unit 114 if it is necessary to do so. The received strength signal S12 converted into a digital signal by the A/D converter 113 is loaded into the control unit C1. The switching controller C1a selects one receiving antenna through which the signal is received at the highest signal strength as the receiving antenna for acquiring the image data based on this received strength signal S12 obtained by sequentially changing over the receiving antennas A1 to An. Furthermore, the switching controller C1a outputs a switching signal S13 for instructing switching to this antenna to the changeover switch SW. Moreover, the control unit C1 records signal strengths received at the respective receiving antennas in the portable recording medium 105 as well as the image data while making the signal strengths correspond to the selected receiving antennas. The signal strengths of the respective receiving antennas thus recorded are used to perform the open-circuit detection with respect to each antenna to be described later, and serve as information for calculating an in-vivo position of the capsule endoscope 103 when the image data is received.

Figure 10:
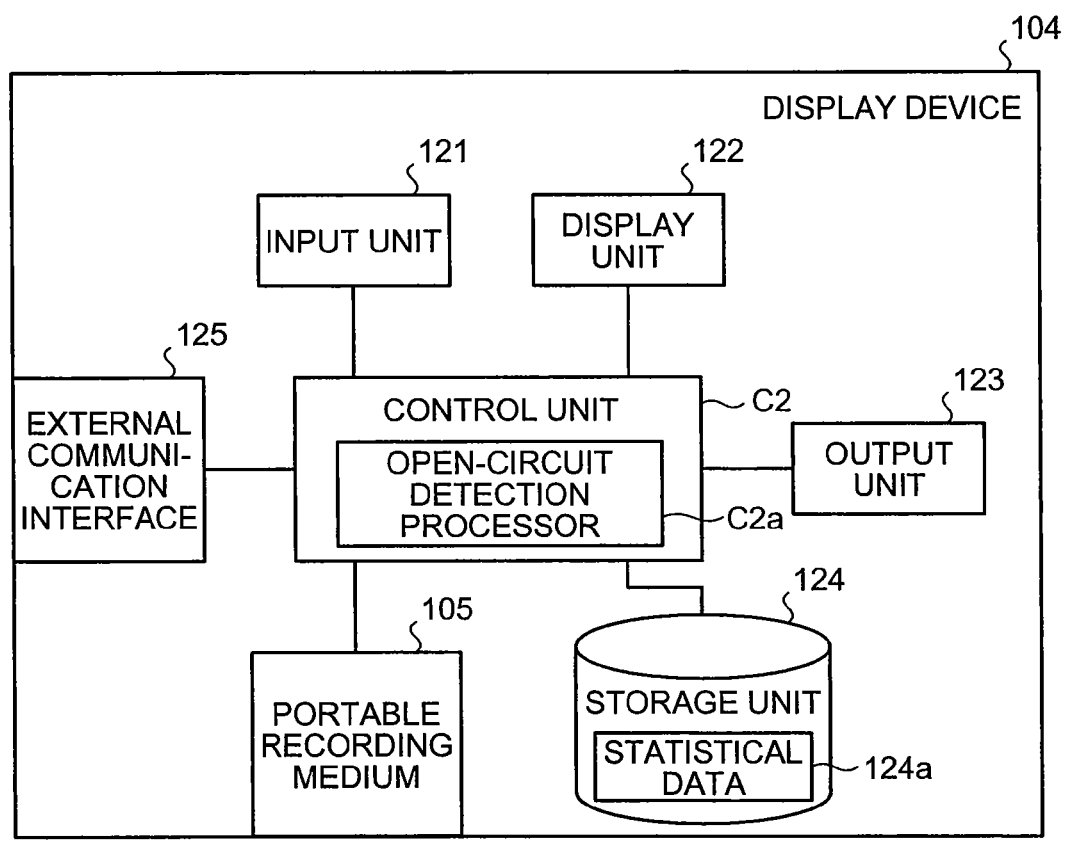
FIG. 10 is a block diagram showing a configuration of a display device shown in FIG. 8.

FIG. 10 is a block diagram showing a configuration of the display device 104. The display device 104, which is realized by a personal computer or the like, further processes the image data recorded in the portable recording medium 105. A patient can be diagnosed and a diagnosis report or the like can be created based on a set of processed image data. As shown in FIG. 10, the display device 104 includes an input unit 121, which is realized by a pointing device such as a keyboard or a mouse and to which various information is input, a display unit 122, which is realized by a liquid crystal display or the like and on and to which various information such as the processed image data is displayed and output, an output unit 123 realized by a printer or the like, a storage unit 124 that stores therein various information including the image data, the detachable portable recording medium 105, an external communication interface 125 that performs a communication/connection processing for communication and connection with an external network, and a control unit C2 realized by a CPU or the like and controlling the respective constituent elements stated above.

The storage unit 124 stores therein statistical data 124a obtained by statistically processing temporal changes in received electric-field strengths of the respective receiving antennas A1 to An based on arrangement of the receiving antennas A1 to An when image data was previously acquired. Furthermore, the control unit C2 includes an open-circuit detecting processor C2a. The open-circuit detecting processor C2a performs the following processings. The open-circuit detecting processor C2a compares the temporal change data on the received electric-field strengths of the respective receiving antennas A1 to An added together with the image data acquired from the portable recording medium 105 with the statistical data 124a. The open-circuit detecting processor C2a detects whether an open-circuit occurs to one of the receiving antennas A1 to An used to acquire this image data or whether a connection failure occurs between the receiving antenna and the changeover switch. Moreover, the open-circuit detecting processor C2a outputs a result of the detection to the display unit 122 or the like.

Figure 11:
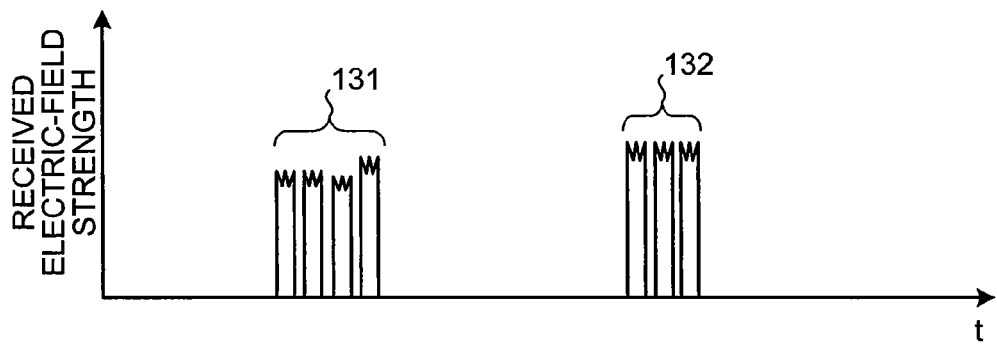
FIG. 11 is a chart showing temporal change in received electric-field strength of a radio signal received by a receiving antenna to which no open-circuit occurs.

In case of one receiving antenna, for example, if no open-circuit occurs thereto, the received electric-field strength of the receiving antenna temporally changes as shown in received electric-field strength profiles 131 and 132 shown in FIG. 11. Averages Av1 to Avn of total received electric-field strengths of the receiving antennas A1 to An are calculated based on a plurality of past temporal changes in received electric-field strengths obtained for the respective receiving antennas A1 to An, and held as the statistical data 124a. The open-circuit detecting processor C2a calculates averages RAv1 to RAvn of currently-obtained, total received electric-field strengths of the respective receiving antennas A1 to An. The open-circuit detecting processor C2a compares the averages Av1 to Avn with the averages RAv1 to RAvn for the respective receiving antennas A1 to An. If the receiving antenna for which the average RAv1 to RAvn is 50% or less of the average Av1 to Avn is present, the open-circuit detecting processor C2a determines that an open-circuit or a connection failure occurs to this receiving antenna, and outputs a result of the determination to the display unit 122.

Figure 12:
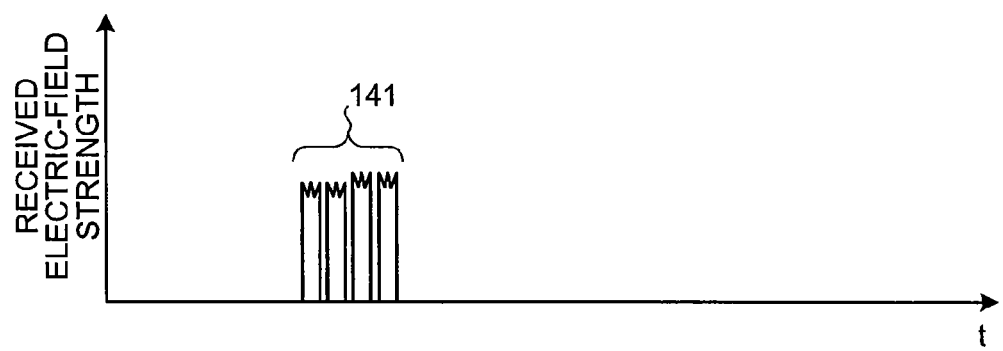
FIG. 12 is a chart showing temporal change in received electric-field strength of a radio signal received by a receiving antenna to which an open-circuit occurs halfway through reception of the radio signal.

It takes about eight hours since the capsule endoscope 103 is inserted into the subject 1 until it is discharged from the subject 1. If an open-circuit occurs to one receiving antenna during that time, this receiving antenna is not selected and a to-be-detected received electric-field strength profile does not appear in a second half of the time as shown in FIG. 12 (that is, a received electric-field strength profile 141 appears only in a first half of the time). As a result, the total received electric-field strength of the receiving antenna to which the open-circuit occurs is reduced. Therefore, as described, it is determined that an open-circuit or a connection failure occurs to the receiving antenna if the average of the total received electric-field strength of the receiving antenna is equal to or lower than the threshold.

The averages Av1 to Avn and Rav1 to RAvn are not necessarily averages in the period in which the capsule endoscope 103 is inserted into the subject 1. For example, averages in a predetermined period retroactive to the time when the capsule endoscope 103 is discharged from the subject 1 can be calculated and compared with one another so as to detect whether an open-circuit or a connection failure occurs.

Figure 13:
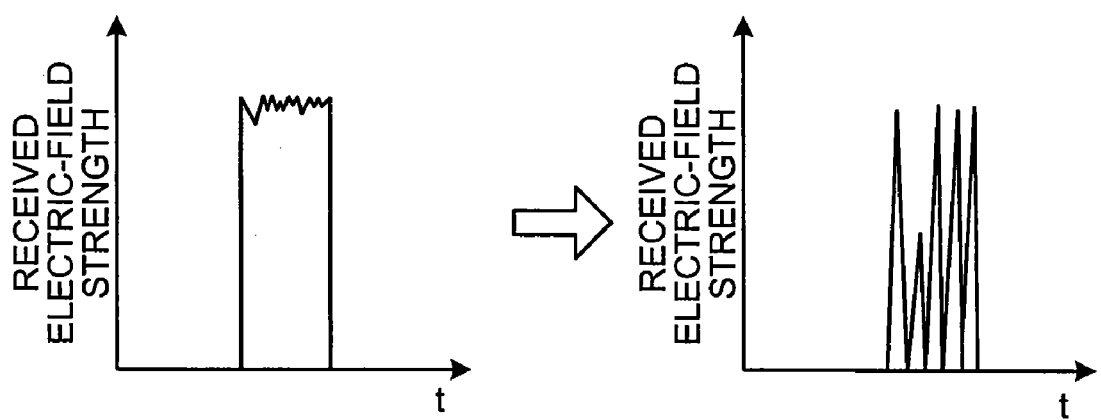
FIG. 13 is a chart showing temporal change in received electric-field strength if a connection failure resulting from an open-circuit occurs.

Moreover, as shown in FIG. 13, if the receiving antenna of which the received electric-field strength has a great temporal change for a predetermined consecutive period of time in a receiving state is present, it is considered that a connection failure occurs to this receiving antenna as a precursor of an open-circuit. Due to this, it can be determined that an open-circuit or a connection failure occurs to the receiving antenna. In this case, the statistical data 124a is not always essential. It is to be noted that whether the received electric-field strength has a great change can be determined by differentiating the temporal change in the received electric-field strength.

Alternatively, typical temporal change profiles of the received electric-field strengths of the respective receiving antennas A1 to An can be stored as the statistical data 124a. The open-circuit detecting processor C2a can calculate correlations between the typical temporal change profiles and currently-obtained temporal change profiles of the respective receiving antennas A1 to An. Furthermore, the open-circuit detecting processor C2 can determine whether an open-circuit or a connection failure occurs to each receiving antenna based on the correlation.

In this fourth embodiment, the previously-obtained statistical data on the received electric-field strengths of the respective receiving antennas is compared with the currently-obtained data on the received electric-field strengths of the respective receiving antennas so as to detect whether an open-circuit or a connection failure occurs to each of the receiving antennas. It is, therefore, possible to facilitate the antennan open-circuit check and enhance the reliability of the antennan open-circuit check. The reliability of the antennan open-circuit check is enhanced because it is possible to detect whether an open-circuit occurs to the receiving antenna for which the occurrence of the open-circuit cannot be detected by the other antennan open-circuit checks.

As described so far, the radio in-vivo information acquiring system according to the fourth embodiment of the present invention is the radio in-vivo information acquiring system including the receiving apparatus that selectively receives a radio signal including in-vivo information according to the received electric-field strengths of the respective receiving antennas through the antennas. In the radio in-vivo information acquiring system, a statistical data holding unit holds the statistical data on the received electric-field strengths of the respective antennas, and an open-circuit detecting unit compares the statistical data with the currently-received data on the received electric-field strengths of the respective antennas to perform an open-circuit detecting processing on each antenna. It is, therefore, advantageously possible to perform the open-circuit detection as part of acquisition of information on examination or the like, and perform the open-circuit detection with respect to each antenna easily within short time.

Fifth Embodiment

A fifth embodiment of the present invention will be described. In the fourth embodiment, the open-circuit detection is performed using the statistical data 124a. In this fifth embodiment, the open-circuit detection is performed based on currently-obtained data on the received electric-field strengths of the respective receiving antennas without using the statistical data 124a.

Namely, the open-circuit detecting processor C2a acquires data on the electric-field strength of each receiving antenna added together with the image data obtained from the portable recording medium 105. If this acquired received electric-field strength of the receiving antenna is almost equal to zero, the open-circuit detecting processor C2a determines that an open-circuit or a connection failure occurs to this receiving antenna.

Alternatively, not the data on the received electric-field strength of each receiving antenna but only selection/switching data on each receiving antenna can be used for the open-circuit detection. Namely, the open-circuit detecting processor C2a determines that an open-circuit or a connection failure occurs to the receiving antenna that has never been selected.

In this fifth embodiment, it is possible to easily detect whether an open-circuit occurs to each receiving antenna without using the statistical data 124a.

Sixth Embodiment

A sixth embodiment of the present invention will be described. In this sixth embodiment, it is detected whether an open-circuit occurs to each receiving antenna based on a size of obtained image data.

The image data obtained through the respective antennas A1 to An is subjected to compression processing such as JPEG by the main receiving unit 102b and recorded in the portable recording medium 105. If a connection failure occurs to one of the receiving antennas A1 to An, noise is mixed into the image data. Due to this, when the image data is compressed, the size of the image data is made larger.

The open-circuit detecting processor C2a determines that an open-circuit or a connection failure occurs to the receiving antenna used when image data is obtained if the size of the obtained image data is out of a predetermined range based on the obtained image data and antenna selection information at the time of obtaining the image data.

If the main receiving unit 102b does not perform the compression processing on the image data, the display device 104 performs the compression processing thereon. In this case, the open-circuit detecting processor C2a performs the open-circuit detection after performing the compression processing on the image data.

In this sixth embodiment, similarly to the fifth embodiment, it is possible to easily detect whether an open-circuit occurs to each receiving antenna.

Seventh Embodiment

A seventh embodiment of the present invention will be described. In this seventh embodiment, the main receiving unit 102b detects whether an open-circuit occurs to each receiving antenna based on an out-of-synchronization condition of an image signal.

A high-frequency signal received by each of the receiving antennas A1 to An is transmitted from the radio unit 102a to the main receiving unit 102b as an image signal in a baseband signal. The main receiving unit 102b generates image data while horizontally synchronizing this image signal with a horizontal synchronization signal and vertically synchronizing the image signal with a vertical synchronization signal.

If an open-circuit or a connection failure occurs to one of the receiving antennas, the image signal cannot be horizontally and vertically synchronized with the horizontal synchronization signal and the vertical synchronization signal. As a result, the image signal is in an out-of-synchronization condition. Therefore, if the total number of out-of-synchronization conditions for each receiving antenna is equal to or larger than a predetermined value or concentration of out-of-synchronization conditions occurs, the open-circuit detecting processor C2a determines that an open-circuit or a connection failure occurs to the receiving antenna. The out-of-synchronization conditions can be counted by the main receiving unit 102b and counts of the out-of-synchronization conditions as well as the antenna selection information are recorded in the portable recording medium 105.

In the seventh embodiment, similarly to the fifth and sixth embodiments, it is possible to easily detect whether an open-circuit occurs to each receiving antenna.

Eighth Embodiment

An eighth embodiment of the present invention will be described. In the eight embodiment, it is detected whether an open-circuit occurs to each receiving antenna based on the number of errors indicated by an error detection signal included in an image signal.

In the eighth embodiment, an error detection signal is included in the image signal transmitted from the capsule endoscope 103, and the main receiving unit 102b performs an error detection processing on the image signal when image data is generating based on this image signal. The main receiving unit 102b records the number of detected errors as well as antenna selection information in the portable recording medium 105.

If the number of detected errors is equal to or larger than a predetermined value or concentration of errors occurs, the open-circuit detecting processor C2a identifies the receiving antenna through which the image data from which the errors are detected based on the antenna selection information. Furthermore, the open-circuit detecting processor C2a determines that an open-circuit or a connection failure occurs to the identified receiving antenna.

In the seventh embodiment, similarly to the fifth to seventh embodiments, it is possible to easily detect whether an open-circuit occurs to each receiving antenna.

In the fourth to eighth embodiments, the display device 104 performs the open-circuit detection. However, the present invention is not limited thereto. Alternatively, an open-circuit detecting processor corresponding to the open-circuit detecting processor C2a can be provided in the main receiving unit 102b, and the open-circuit detecting processor can record a result of the open-circuit detection in the portable recording medium 105. In this case, the switching controller C1a controls the changeover switch SW to exclude the antenna to which the open-circuit occurs from subsequent selection/switching target antennas so as not to select this antenna. Further, if it is detected that an open-circuit occurs, the detection result can be displayed on the display unit 114 or the like or notified. By doing so, unnecessary verifications can be promptly discovered and, measures for avoiding the unnecessary verifications can be taken by replacing the receiving antenna for which it is detected that the open-circuit occurs or the entire radio unit 102a.

In the fifth to eighth embodiments, the statistical data is not specially used. However, a threshold for determination as to whether an open-circuit or a connection failure occurs can be statistically calculated based on data obtained when the receiving antenna to which no open-circuit or connection failure occurs is used and data obtained when the receiving antenna to which an open-circuit or a connection failure occurs.

Ninth Embodiment

A preferred embodiment of an open-circuit detecting method according to the present invention will be described with reference to the drawings. It is to be noted that the present invention is not limited by the ninth embodiment.

The in-vivo information acquiring system for inserting the capsule endoscope into the body of the subject and for acquiring intra-subject image data will first be described. An open-circuit detecting method for each of the receiving antennas included in the receiving apparatus that receives a radio signal from the capsule endoscope in the in-vivo information acquiring system (that is, the open-circuit detecting method according to the ninth embodiment of the present invention) will next be described.

Figure 14:
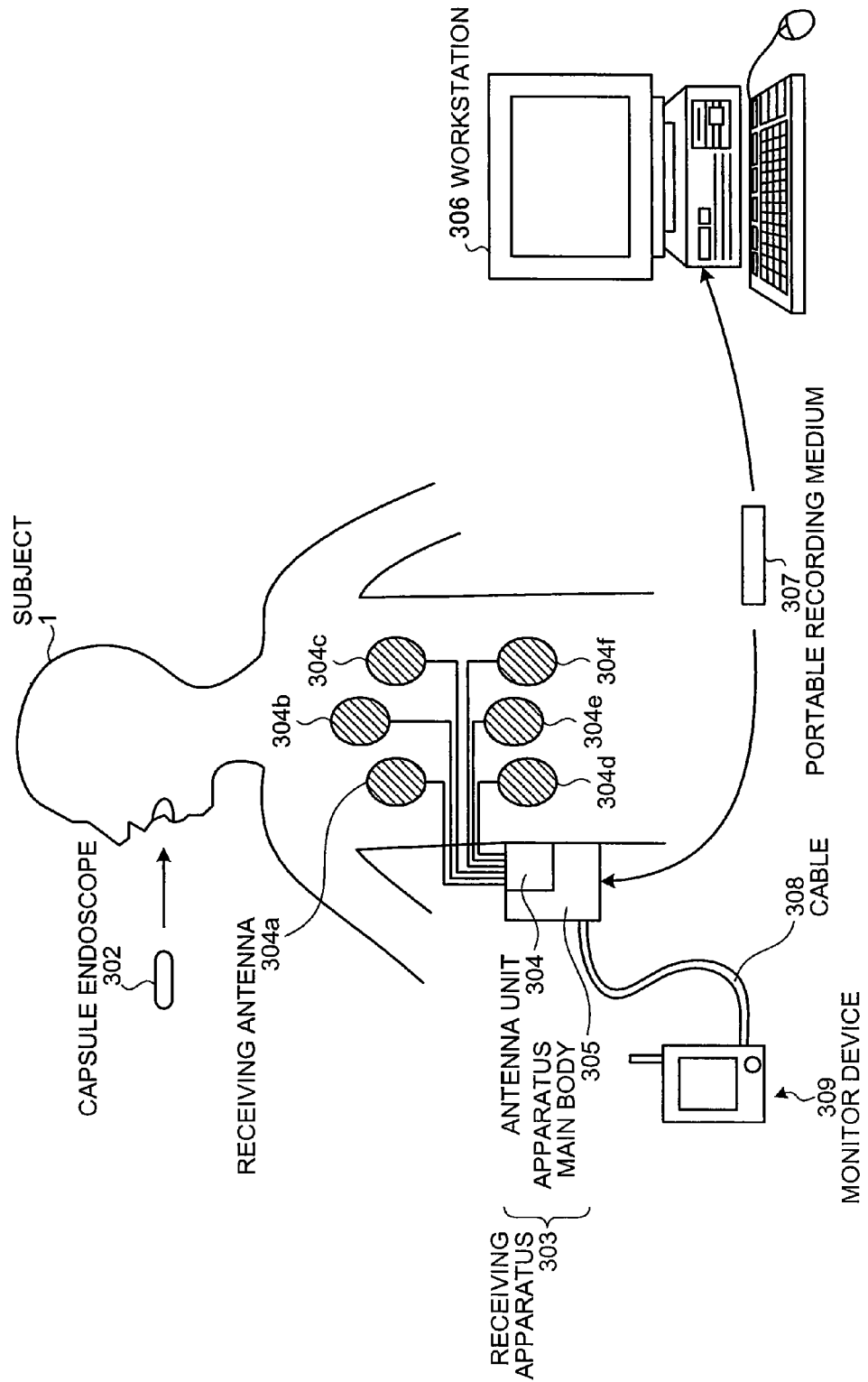
FIG. 14 is a pattern diagram typically showing an example of a configuration of an in-vivo information acquiring system according to a ninth embodiment of the present invention.

FIG. 14 is a pattern diagram typically showing an example of a configuration of an in-vivo information acquiring system according to the ninth embodiment. As shown in FIG. 14, the in-vivo information acquiring system according to the ninth embodiment includes a capsule endoscope 302 that moves along a passing route in the body of the subject 1 and that picks up an in-vivo image of the subject 1, a receiving apparatus 303 that receives a radio signal including the image data picked up by the capsule endoscope 302, a workstation 306 that displays the in-vivo image of the subject 1 based on the image data picked up by the capsule endoscope 302, and a portable recording medium 307 for transmitting and receiving data between the receiving apparatus 303 and the workstation 306. Moreover, this in-vivo information acquiring system includes a portable monitor device 309 connected to the receiving apparatus 303 through a cable 308 and sequentially displaying the image data acquired by the receiving apparatus 303.

The capsule endoscope 302 includes a capsule casing structure easily insertable into the body of the subject 1. Furthermore, the capsule endoscope 302 includes an imaging function of picking up the in-vivo image of the subject 1 and a radio communication function of transmitting the image data obtained by picking up the in-vivo image of the subject 1 to the receiving apparatus 303 outside of the capsule endoscope 302. Specifically, the capsule endoscope 302 is swallowed by the subject 1 to thereby pass through the esophagus, and moves in the body cavity according to the peristaltic movement of the alimentary lumen. At the same time, the capsule endoscope 302 sequentially picks up images of the interior of the body cavity of the subject 1 and sequentially transmits radio signals each including the obtained in-vivo image data on the subject 1 to the receiving apparatus 303.

The receiving apparatus 303 receives the radio signal from the capsule endoscope 302 inserted into the body of the subject 1, and acquires the image data picked up by the capsule endoscope 302 based on the radio signal. Specifically, the receiving apparatus 303 is realized by using an antenna unit 304 to which a plurality of receiving antennas 304a to 304f for receiving the radio signal from the capsule endoscope 302 are connected, and an apparatus main body 305 that performs various processings for sequentially acquiring the image data. The receiving apparatus 303 receives the radio signal from the capsule endoscope 302 through one of the receiving antennas 304a to 304f, demodulates this radio signal into an image signal, and acquires the image data picked up by the capsule endoscope 302 based on the obtained image signal. In this case, the receiving apparatus 303 sequentially stores the acquired image data picked up by the capsule endoscope 302 in the portable recording medium 307 detachably inserted into the apparatus main body 305.

Each of the receiving antennas 304a to 304f is realized by using, for example, a loop antenna, and receives the radio signal transmitted from the capsule endoscope 302. The receiving antennas 304a to 304f are arranged to be distributed to predetermined positions on the body surface of the subject 1, e.g., positions corresponding to the passing route of the capsule endoscope 302 as shown in FIG. 14. The receiving antennas 304a to 304f can be arranged at predetermined positions of a jacket which the subject 1 wears, respectively. In this case, by causing the subject 1 to wear this jacket, the receiving antennas 304a to 304f are arranged at the predetermined positions on the body surface of the subject 1, respectively. It suffices that one or more receiving antennas are arranged on the subject 1 or preferably a plurality of receiving antennas are arranged to be distributed. In this case, the number of arranged antennas is not limited to six.

The workstation 306 is to display the in-vivo image of the subject 1 picked up by the capsule endoscope 302, and displays an image of an organ or the like in the body of the subject 1 based on the image data or the like obtained through the portable recording medium 307 (that is, the image picked up by the capsule endoscope 302). Furthermore, the workstation 306 includes a processing function for allowing a doctor or a nurse to diagnose the subject 1 by observing the image of the organ or the like in the body of the subject 1 using the capsule endoscope 302. Moreover, the workstation 306 includes an initialization processing function of initializing the receiving apparatus 303 as the receiving apparatus that carries out a capsule endoscopy examination on the subject 1.

The portable recording medium 307 is a portable recording media such as a compact flash (registered trademark). The portable recording medium 307 is detachable from the apparatus main body 305 of the receiving apparatus 303 or the workstation 306, and includes a structure capable of outputting and recording data when being attached to the apparatus main body 305 or the workstation 306. Specifically, when being attached to the receiving apparatus 303, the portable recording medium 307 sequentially stores therein image data or the like from the capsule endoscope 302 acquired by the receiving apparatus 303. Further, after the capsule endoscope 302 is discharged from the subject 1, the portable recording medium 307 is detached from the receiving apparatus 303 and attached to the workstation 306. In this case, the workstation 306 can load therein various data such as the in-vivo image data or the like on the subject 1 stored in the portable recording medium 307 attached thereto.

By causing the portable recording medium 307 to mediate between the receiving apparatus 303 and the workstation 306 to transmit and receive data therebetween, the subject 1 can freely act while carrying the receiving apparatus 303 even when the capsule endoscope 302 is moving in the body of the subject 1, differently from the instance in which the receiving apparatus 303 is wired-connected to the workstation 306 by a communication cable or the like.

The monitor device 309 is to display the image data acquired by the receiving apparatus 303 from the capsule endoscope 302 at real time. Specifically, the monitor device 309 is connected to the apparatus main body 305 through a cable 308, and receives the image data acquired by the receiving apparatus 303 from the receiving apparatus 303. The monitor device 309 sequentially monitor-displays the image data thus received from the receiving apparatus 303. Namely, the monitor device 309 acquires the image data picked up by the capsule endoscope through the receiving apparatus 303, and sequentially monitor-displays the acquired image data. Furthermore, the monitor device 309 includes the radio communication function of receiving the radio signal from the capsule endoscope without via the receiving apparatus 303, and acquires the image data picked up by the capsule endoscope 302 based on the received radio signal. In this case, the monitor device 309 sequentially monitor-displays the image data picked up by the capsule endoscope 302 acquired without via the receiving apparatus 303.

Figure 15:
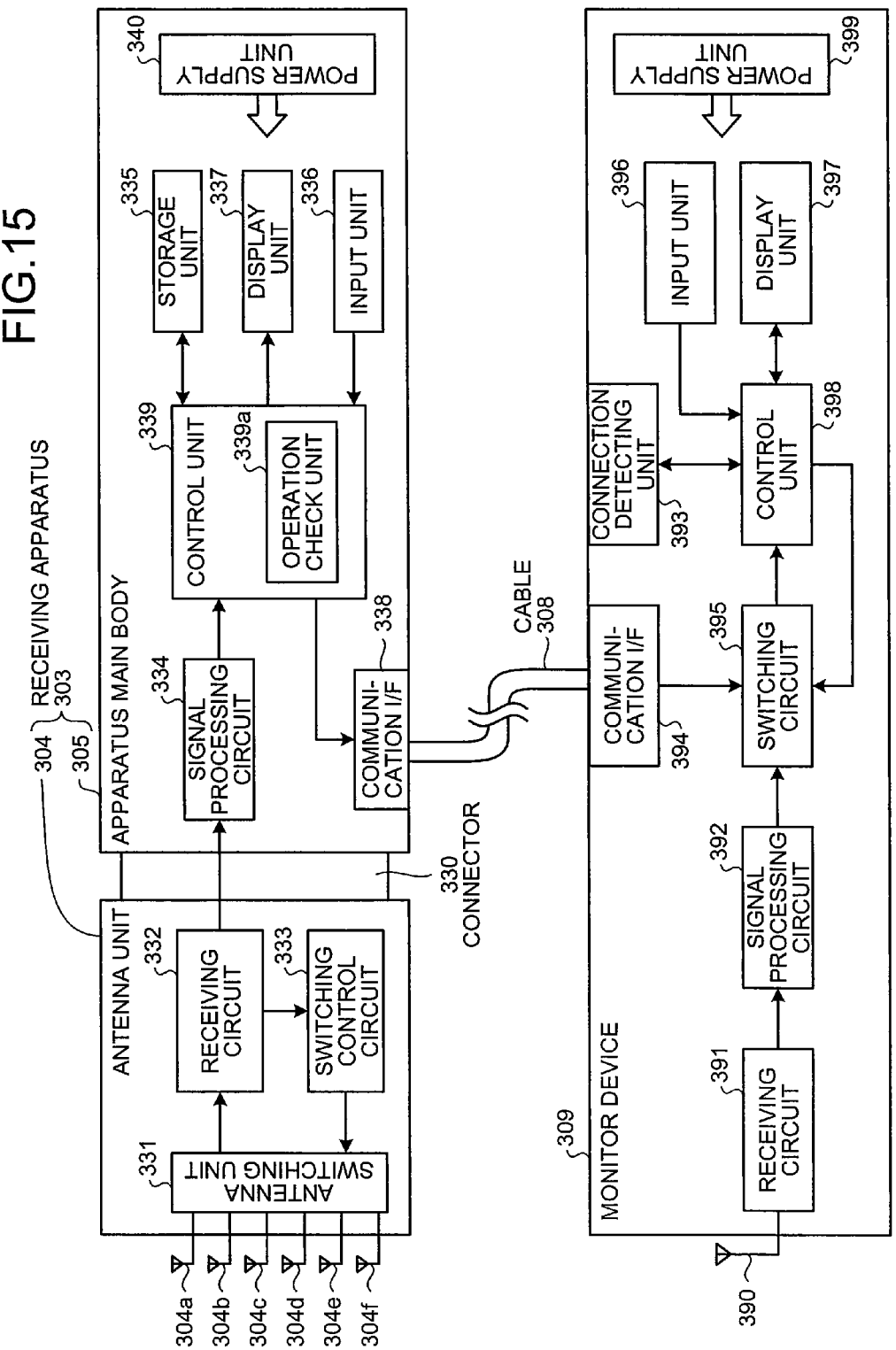
FIG. 15 is a block diagram typically showing an example of configurations of a receiving apparatus and a monitor device connected to each other through a cable, respectively.

Configurations of the receiving apparatus 303 and the monitor device 309 will next be described. FIG. 15 is a block diagram typically showing an example of the configurations of the receiving apparatus 303 and the monitor device 309 connected to each other through the cable 308. Referring to FIG. 15, the configuration of the receiving apparatus 303 will first be described, and that of the monitor device 309 will next be described.

As shown in FIG. 15, the receiving apparatus 303 is formed by connecting the antenna unit 304 to the apparatus main body 305 through a connector 330. As described, the antenna unit 304 includes an antenna switching unit 331, a receiving circuit 332, and a switching control circuit 333. The antenna switching unit 331, to which the receiving antennas 304a to 304f are connected, switches to one receiving antenna suitable for receiving the radio signal from among the receiving antennas 304a to 304f. The receiving circuit 332 demodulates the radio signal received through one of the receiving antennas 304a to 304f into the image signal, and receives the received electric-field strength of this radio signal. The switching control circuit 333 controls the antenna switching unit 331 to perform an antenna switching operation based on the received electric-field strength detected by the receiving circuit 332.

The apparatus main body 305 includes a signal processing circuit 334, a storage unit 335, an input unit 336, and a display unit 337. The signal processing circuit 334 generates the image data picked up by the capsule endoscope 302 based on the image signal demodulated by the receiving circuit 332. The storage unit 335 stores therein the image data or the like generated by the signal processing circuit 334. The input unit 336 receives instruction information on an instruction to start the receiving apparatus 303 or to cause the receiving apparatus 303 to perform various operations. The display unit 337 displays information or the like on the subject 1. Furthermore, the apparatus main body 305 includes a communication interface (I/F) 338 for transmitting the image data or the like to the monitor device 309 through the cable 308, a control unit 339 that controls driving of the respective constituent elements of the receiving apparatus 303, and a power supply unit 340 that supplies driving power to the respective constituent elements of the receiving apparatus 303.

The antenna switching unit 331 is to perform the antenna switching operation for electrically connecting one switched antenna from among the receiving antennas 304a to 304f to the receiving circuit 332. In this case, the antenna switching unit 331 performs the antenna switching operation under control of the switching control circuit 333, and electrically connects one of the receiving antennas 304a to 304f suitable for receiving the radio signal from the capsule endoscope 302 to the receiving circuit 332. The antenna switching unit 331 outputs the radio signal from the capsule endoscope 302 received through the receiving antenna selected from among the receiving antennas 304a to 304f to the receiving circuit 332.

The receiving circuit 332 includes a demodulation processing function of demodulating the radio signal input from the antenna switching unit 331 into a baseband signal, and a received-strength detection function of detecting the received electric-field strength of this radio signal. Specifically, the receiving circuit 332 performs a demodulation processing or the like on the radio signal input from the antenna switching unit 331, thereby demodulating the radio signal into the image signal that is the baseband signal. This image signal is the baseband signal including the image data picked up by the capsule endoscope 302. The receiving circuit 332 outputs the obtained image signal to the signal processing circuit 334. Furthermore, the receiving circuit 332 detects the received electric-field strength of the radio signal, and outputs a signal indicating the detected received electric-field strength, e.g., RSSI (Received Signal Strength Indicator) to the switching control circuit 333.

The switching control circuit 333 is to control the antenna switching operation performed by the antenna switching unit 331. Specifically, the switching control circuit 333 selects the receiving antenna with which the received electric-field strength of the radio signal is the highest from among the receiving antennas 304a to 304f based on the signal (e.g., RSSI signal) input from the receiving circuit 332 and indicating the received electric-field strength. Moreover, the switching control circuit 333 controls the antenna switching operation performed by the antenna switching unit 331 so as to electrically connect the selected receiving antenna to the receiving circuit 332.

The signal processing circuit 334 is to generate the image data based on the image signal demodulated by the receiving circuit 332. Specifically, the signal processing circuit 334 performs a predetermined image processing or the like on the image signal demodulated by the receiving circuit 332, and generates the image data picked up by the capsule endoscope 302 based on this image signal. The signal processing circuit 334 outputs the obtained image data to the control unit 339.

The storage unit 335, to which the portable recording medium 307 is detachably attached, sequentially stores the data for which the storage unit 335 is instructed by the control unit 339 to store, e.g., the image data generated by a signal processing circuit 34 in the portable recording medium 307. Alternatively, the storage unit 335 can be constituted so that the storage unit 335 itself accumulates therein various information such as the image data by including a memory IC such as a RAM or a flash memory.

The input unit 336 is realized by using an input button for receiving instruction information on an instruction to the control unit 339. The input unit 336 inputs various instruction information such as an instruction to display information on the subject 1 on the display unit 337, to the control unit 339 according to a user's input operation. The display unit 337, which is realized by using a thin display such as a liquid-crystal display device or an organic EL panel, displays information instructed by the control unit 339 to display, e.g., the information on the subject 1. The display unit 337 can be constituted to include an information input function such as a touch panel so as to input the instruction information to the control unit 339 in place of the input unit 336. In this case, the receiving apparatus 303 does not need to include the input unit 336.

The communication I/F 338 is to transmit the image data acquired by the receiving apparatus 303 to the monitor device 309. Specifically, the communication I/F 338 is connected to the monitor device 309 through the cable 308, and transmits the image data generated by the signal processing circuit 34 (that is, the image data picked up by the capsule endoscope 302) to the monitor device 309.

The control unit 339 is realized by using a CPU that executes a processing program, a ROM that stores therein the processing program or the like, and a RAM that stores therein operation parameters or input information to be input to the control unit 339, and controls the driving of the respective constituent elements of the receiving apparatus 303. In this case, the control unit 339 controls input/output of information among the respective constituent elements, and controls a data storage operation and a data read operation with respect to the storage unit 335 (specifically, the portable recording medium 307), a display operation performed by the display unit 337, an operation for transmitting the image data to the monitor device 309 through the communication I/F 338, and the like. Such a control unit 339 performs various processings based on the instruction information input by the input unit 336.

Moreover, the control unit 339 includes an operation check unit 339a. The operation check unit 339a performs a self-diagnostic processing for confirming whether each constituent element of the receiving apparatus 303 operates normally using, for example, the instruction information input from the input unit 336 as a trigger. In this case, the operation check unit 339a determines whether connection states among the antenna switching unit 331, the receiving circuit 332, the switching control circuit 333, the signal processing circuit 334, the storage unit 335, the input unit 336, the display unit 337, the communication I/F 338, the control unit 339, and the power supply unit 340 are normal, respectively, and thereby diagnoses whether each of the constituent elements is normally operable. Furthermore, the operation check unit 339a determines whether the monitor device 309 connected to the receiving apparatus 303 through the cable 308 normally performs a monitor display operation, that is, whether the monitor device 309 can monitor-display the image data generated by the signal processing circuit 334. The control unit 339 causes a diagnosis result of the operation check unit 339a to be displayed on the display unit 337.

The power supply unit 340 supplies driving power to each constituent element of the receiving apparatus 303 if a power switch (not shown) provided on the apparatus main body 305 is switched to be turned on. Examples of the power supply unit 340 include a dry battery, a lithium-ion secondary battery, and a nickel-hydrogen battery. Furthermore, the power supply unit 340 can be a rechargeable power supply unit.

The configuration of the monitor device 309 will next be described. As shown in FIG. 15, the monitor device 309 includes a receiving antenna 390, a receiving circuit 391, and a signal processing circuit 392. The receiving antenna 390 is an antenna for receiving the radio signal from the capsule endoscope 302. The receiving circuit 391 demodulates the radio signal received through the receiving antenna 390 into an image signal. The signal processing circuit 392 generates the image data picked up by the capsule endoscope 302 based on the image signal demodulated by the receiving circuit 391. The monitor device 309 also includes a connection detector 393, a communication I/F 394, and a switching circuit 395. The connection detector 393 detects whether the receiving apparatus 303 is connected to the monitor device 309 through the cable 308. The communication I/F 394 is an interface for receiving the image data from the receiving apparatus 303 through the cable 308. The switching circuit 395 outputs the image data from the communication I/F 394 to a control unit 398 if the receiving apparatus 303 is connected to the monitor device 309, and outputs the image data from the signal processing circuit 392 to the control unit 398 if the receiving apparatus 303 is not connected to the monitor device 309. The monitor device 309 further includes an input unit 396, a display unit 397, the control unit 398, and a power supply unit 399. The input unit 396 inputs instruction information on an instruction to a control unit 96, to the control unit 96. The display unit 397 monitor-displays the image data or the like. The control unit 398 controls driving of the respective constituent elements of the monitor device 309. The power supply unit 399 supplies driving power to the respective constituent elements of the monitor device 309.

The receiving antenna 390, the receiving circuit 391, and the signal processing circuit 392 function to receive the radio signal from the capsule endoscope 302 and to acquire the image data picked up by the capsule endoscope 302 based on this radio signal if the receiving apparatus 303 is not connected to the monitor device 309. Specifically, the receiving antenna 390 receives the radio signal from the capsule endoscope 302, and outputs the received radio signal to the receiving circuit 391. The receiving circuit 391 demodulates the radio signal received through the receiving antenna 390 into the image signal, and outputs the obtained image signal to the signal processing circuit 392. The signal processing circuit 392 generates the image data picked up by the capsule endoscope 302 based on the image signal demodulated by the receiving circuit 391, and outputs the obtained image data to the switching circuit 395.

By including the receiving antenna 390, the receiving circuit 391, and the signal processing circuit 392 thus configured, the monitor device 309 can acquire the image data picked up by the capsule endoscope 302 without via the receiving apparatus 303, and monitor-display this image data on the display unit 397.

The connection detector 393 functions to detect whether the receiving apparatus 303 is connected to the monitor device 309. Specifically, the connection detector 393 detects that the receiving apparatus 303 is connected to the monitor device 309 by detecting electrical continuation accompanying the connection between the receiving apparatus 303 and the monitor device 309 through the cable 308. If detecting that the receiving apparatus 303 is connected to the monitor device 309, the connection detector 393 outputs a detection result indicating that this connection is detected to the control unit 398.

The communication I/F 394 functions to receive the image data transmitted from the receiving apparatus 303 through the cable 308. Specifically, the communication I/F 394 is connected to the communication I/F 338 of the receiving apparatus 303 through the cable 308, and the image data output from this communication I/F 338, i.e., the image data acquired by the receiving apparatus 303 is input to the communication I/F 394. The communication I/F 394 outputs the obtained image data to the switching circuit 395.

The switching circuit 395 performs the switching operation for electrically connecting the control unit 398 to either the signal processing circuit 392 or the communication I/F 394 according to whether the receiving apparatus and the monitor device are connected/unconnected to each other. Specifically, if the receiving apparatus 303 is connected to the monitor device 309, the switching circuit 395 electrically connects the communication I/F 394 to the control unit 398 under control of the control unit 398. If the receiving apparatus 303 is unconnected to the monitor device 309, the switching circuit 395 electrically connects the signal processing circuit 392 to the control unit 398 under control of the control unit 398. Namely, if the receiving apparatus 303 is connected to the monitor device 309, the switching circuit 395 outputs the image data from the communication I/F 394 (the image data acquired by the receiving apparatus 303) to the control unit 398. If the receiving apparatus 303 is unconnected to the monitor device 309, the switching circuit 395 outputs the image data generated by the signal processing circuit 392 to the control unit 398.

The input unit 396 is realized by using an input button for inputting the instruction information on an instruction to the control unit 398, to the control unit 398. The input unit 396 inputs instruction information or the like such as an instruction to start driving the respective constituent elements according to a user's input operation, to the control unit 398. The display unit 397, which is realized by using a thin display such as a liquid-crystal display device or an organic EL panel, displays information instructed by the control unit 398 to display, e.g., the image data received from the receiving apparatus 303 through the cable 308 or the image data acquired not via the receiving apparatus 303. The display unit 397 includes an information input function such as a touch panel so as to input the instruction information to the control unit 398.

The control unit 398 is realized by using a CPU that executes a processing program, a ROM that stores therein the processing program or the like in advance, and a RAM that stores therein operation parameters or input information to be input to the control unit 339, and controls driving of the respective constituent elements of the monitor device 309. In this case, the control unit 398 controls input/output of information among the respective constituent elements, and controls a monitor display operation performed by the display unit 397, a detection operation performed by the connection detector 393 and the like.

Furthermore, the control unit 398 controls the above-stated switching operation performed by the switching circuit 395. Specifically, if receiving the detection result indicating that the receiving apparatus 303 is connected to the monitor device 309 from the connection detector 393, the control unit 398 controls the switching operation performed by the switching circuit 395 to electrically connect the communication I/F 394 to the control unit 398. If not receiving the detection result indicating that the receiving apparatus 303 is connected to the monitor device 309 from the connection detector 393, the control unit 398 controls the switching operation performed by the switching circuit 395 to electrically connect the signal processing circuit 392 to the control unit 398.

The power supply unit 399 supplies the driving power to the respective constituents of the monitor device 309 if a power switch (not shown) provided on the monitor device 309 is switched to be turned on. Examples of the power supply unit 399 include a dry battery, a lithium-ion secondary battery, and a nickel-hydrogen battery. Furthermore, the power supply unit 399 can be a rechargeable power supply unit.

The monitor device 309 adopting such a configuration is connected to the receiving apparatus 303 through the cable 308, whereby the monitor device 309 functions to receive the image data picked up by the capsule endoscope 302 through the receiving apparatus 303, and to sequentially displays this received image data, i.e., the image data acquired by the receiving apparatus 303 at real time.

An open-circuit detection with respect to each of the receiving antennas 304a to 304f provided on the receiving apparatus 303 of the in-vivo information acquiring system stated above will be described. An open-circuit detecting device employed to perform the open-circuit detection with respect to the receiving antennas 304a to 304f will first be described, and an open-circuit detecting method for the receiving antennas 304a to 304f using this open-circuit detecting device will next be described.

Figure 16:
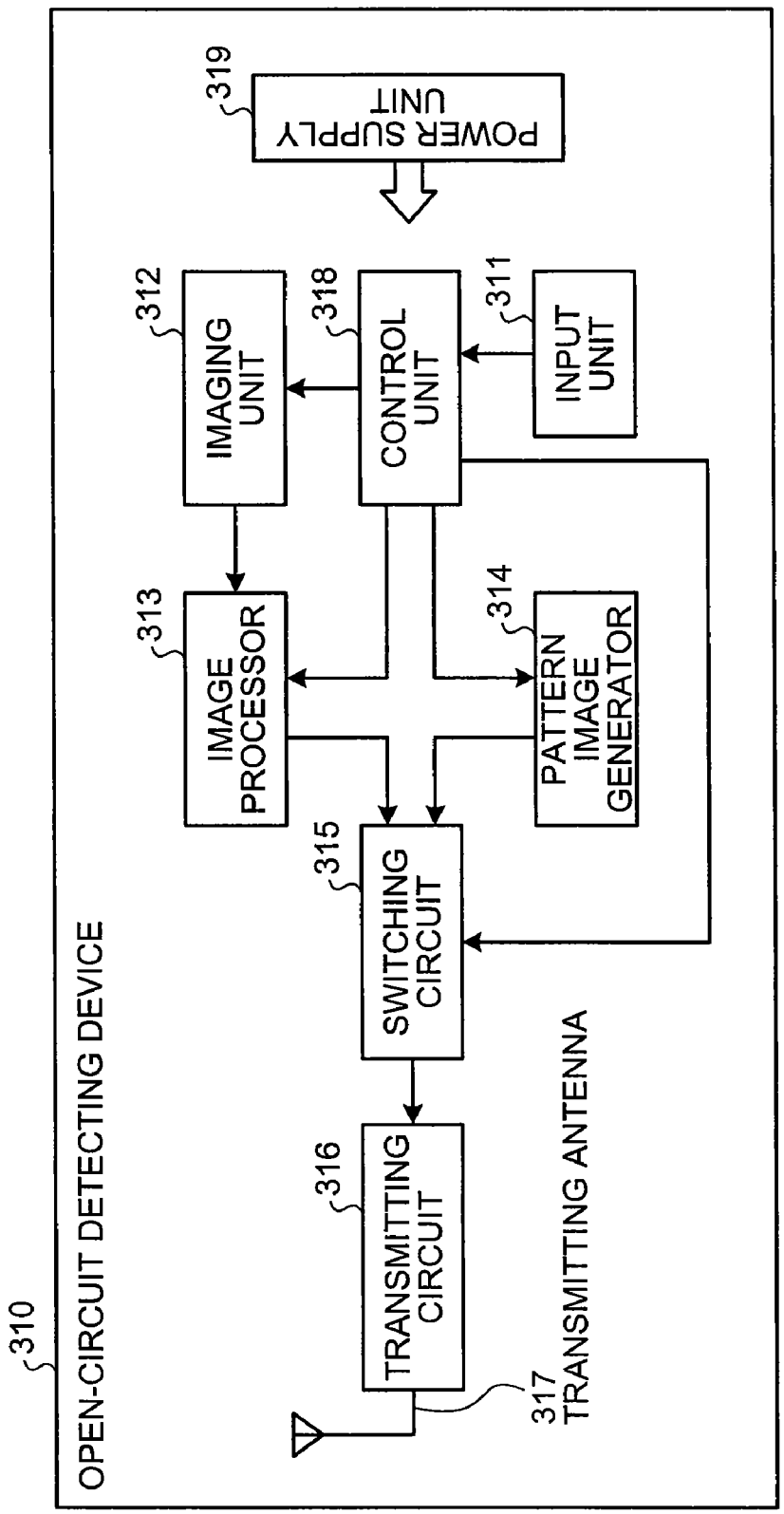
FIG. 16 is a block diagram typically showing an example of a configuration of an open-circuit detecting device for performing an open-circuit detection with respect to a receiving antenna based on an open-circuit detecting method according to the ninth embodiment of the present invention.

FIG. 16 is a block diagram typically showing an example of a configuration of the open-circuit detecting device that performs an open-circuit detection with respect to each of the receiving antennas based on the open-circuit detecting method according to the ninth embodiment of the present invention. As shown in FIG. 16, this open-circuit detecting device 310 includes an input unit 311, an imaging unit 312, an image processor 313, and a pattern image generator 314. The input unit 311 receives various instruction information. The imaging unit 312 picks up a natural image to be transmitted so as to perform an open-circuit detection with respect to each of the receiving antennas. The image processor 313 generates an image signal including the natural image picked up by the imaging unit 312. The pattern image generator 314 generates an image signal including a pattern signal in a preset, predetermined pattern. The open-circuit detecting device 310 also includes a switching circuit 315, a transmitting circuit 316, and a transmitting antenna 317. The switching circuit 315 outputs the image signal from the image processor 313 or the image signal from the pattern image generator 314 to the transmitting circuit 316. The transmitting circuit 316 modulates the image signal input through the switching circuit 315 to generate a radio signal for a test (hereinafter, "test radio signal"). The transmitting antenna 317 is an antenna for outputting the test radio signal generated by the transmitting circuit to the outside. Furthermore, the open-circuit detecting device 310 includes a control unit 318 that controls driving of the constituent element of the open-circuit detecting device 310, and a power supply unit 319 that supplies driving power to the respective constituent elements of the open-circuit detecting device 310.

The input unit 311, which is realized by using an input button for inputting instruction information on instructions to the control unit 318. The input unit 311 inputs, to the control unit 318, instructions such as an instruction to start outputting the test radio signal to the outside and an instruction to switch a test image output by the test radio signal to the natural image or to the pattern image according to a user's input operation. It is to be noted that this test image is either the natural image or the pattern image.

The imaging unit 312 picks up the natural image transmitted as the test image used to perform the open-circuit detection with respect to each of the receiving antennas. Specifically, the imaging unit 312 is realized by using a light-emitting device such as an LED, an imaging device such as a CCD or a CMOS, and an optical system such as a lens. In this case, the imaging unit 312 receives a reflected light by the object, which reflected light is a reflected light of an illumination light irradiated to a desired imaging field of view, and photoelectrically converts the received reflected light, thereby picking up a desired natural image. The imaging unit 312 outputs image data on the obtained natural image to the image processor 313.

The image processor 313 generates an image signal including the image data on the natural image picked up by the imaging unit 312. Specifically, the image processor 313 performs a predetermined signal processing on the image data input from the imaging unit 312, and generates the image signal including the image data on the natural image. The image processor 313 outputs the obtained image signal to the switching circuit 315.

The pattern image generator 314 generates an image signal including the pattern image in the preset, predetermined pattern as the image data. Specifically, the pattern image generator 314 generates the pattern image in the pattern instructed by the control unit 318 from among a plurality of types of preset patterns, and generates the image signal including the image data on the generated pattern image. The pattern image generator 314 outputs the obtained image signal to the switching circuit 315. Examples of this pattern image include a color bar formed by predetermined colors, a gray scale, a gradation scale based on a predetermined ramp waveform, a white image, and a black image.

The switching circuit 315 switches the test image included in the test radio signal to be transmitted to the outside, to either the natural image or the pattern image. Specifically, the switching circuit 315 performs a switching operation for electrically connecting either the image processor 313 or the pattern image generator 314 to the transmitting circuit 316 under control of the control unit 318 based on the instruction information input by the input unit 311. In this case, the switching circuit 315 outputs either the image signal from the image processor 313 (that is, the image signal including the natural image) or the image signal from the pattern image generator 314 (that is, the image signal including the pattern image) to the transmitting circuit 316 by performing the switching operation under control of the control unit 318.

The transmitting circuit 316 is to modulate the image signal including the image data on the test image into the test radio signal. Specifically, the transmitting circuit 316 performs a modulation processing, a power amplification processing and the like on the image signal received either from the image processor 313 or the pattern image generator 314 through the switching circuit 315, thereby modulating this image signal into the test radio signal. The transmitting circuit 316 outputs the obtained test radio signal to the transmitting antenna 317. The transmitting antenna 317 outputs the test radio signal generated by the transmitting circuit 316 to the outside. It is preferable that the transmitting antenna 317 transmits the test radio signal almost equal in frequency band to the radio signal transmitted by the capsule endoscope 302.

The control unit 318 is realized by using a CPU that executes a processing program, a ROM that stores therein the processing program or the like, and a RAM that stores therein operation parameters or input information to be input to the control unit 398, and controls driving of the respective constituent elements of the open-circuit detecting device 310. In this case, the control unit 318 controls input/output of information among the respective constituent elements, and controls driving of the respective constituent elements based on the instruction information from the input unit 311. For example, the control unit 318 controls an imaging operation performed by the imaging unit 312 based on an imaging start instruction from the input unit 311, and controls an image signal generation operation performed by the image processor 313. Alternatively, the control unit 318 controls a pattern image generation operation and an image signal generation operation performed by the pattern image generator 314 based on a pattern-image generation instruction from the input unit 311. Furthermore, the control unit 318 controls the switching operation performed by the switching circuit to electrically connect the image processor 313 to the transmitting circuit 316 based on a natural-image transmission instruction from the input unit 311, and controls the transmitting circuit 316 to modulate the image signal generated by the image processor 313 into the test radio signal and to transmit the modulated test radio signal to the outside. Alternatively, the control unit 318 controls the switching operation performed by the switching circuit to electrically connect the pattern image generator 314 to the transmitting circuit 316, and controls the transmitting circuit 316 to modulate the image signal generated by the pattern image generator 314 into the test radio signal and to transmit the modulated test radio signal to the outside.

The power supply unit 319 supplies driving power to each constituent element of the open-circuit detecting device 310 if a power switch (not shown) provided on the open-circuit detecting device 310 is switched to be turned on. Examples of the power supply unit 319 include a dry battery, a lithium-ion secondary battery, and a nickel-hydrogen battery. Furthermore, the power supply unit 319 can be a rechargeable power supply unit.

The open-circuit detecting device 310 adopting such a configuration can transmit the test radio signal including a desired test image as the image data. By employing the open-circuit detecting device 310 that transmits such a test radio signal, it is possible to detect whether an open-circuit occurs to each of the receiving antennas 304a to 304f provided on the receiving apparatus 303.

Figure 17:
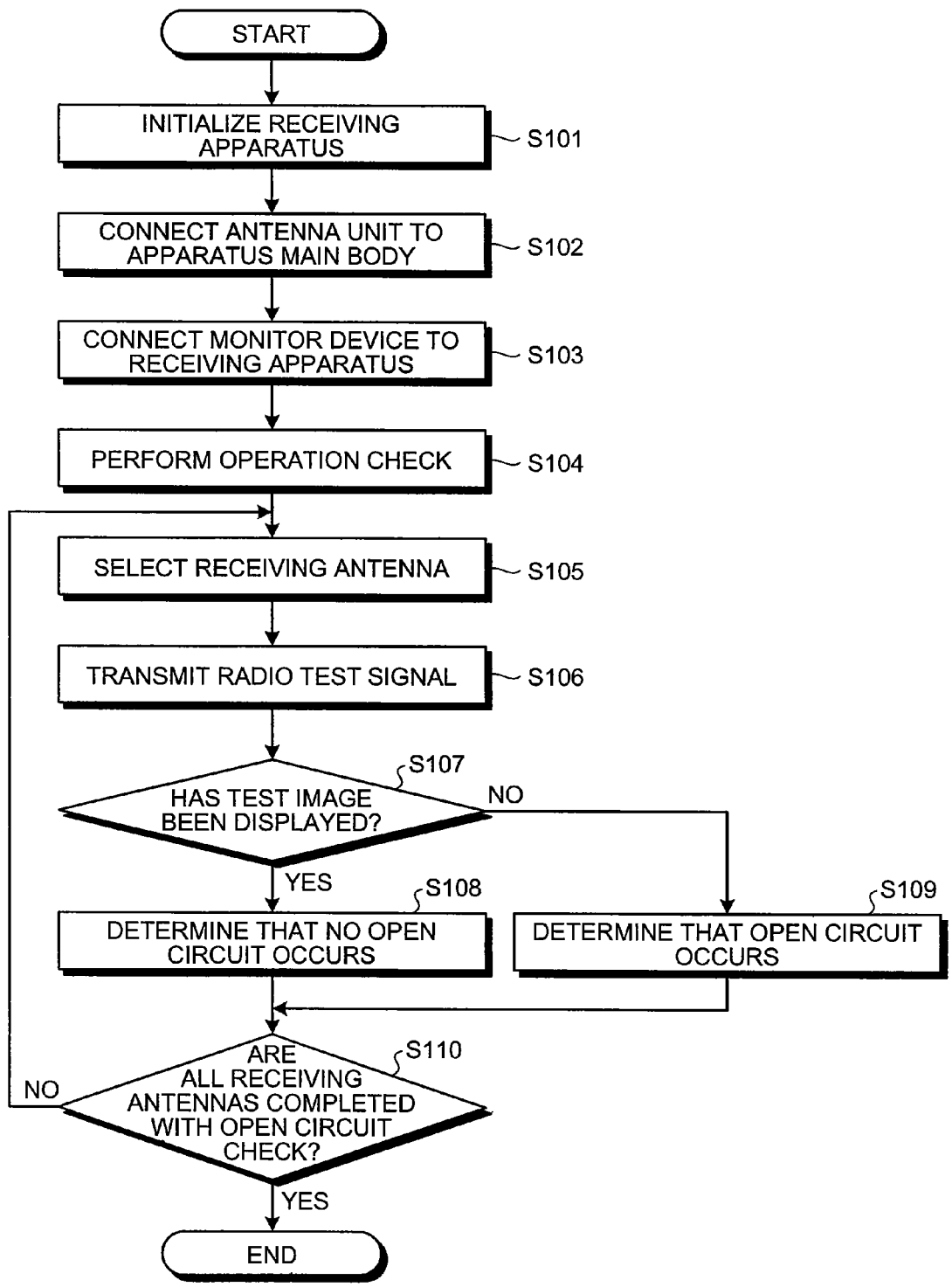
FIG. 17 is a flowchart showing an example of the open-circuit detecting method according to the ninth embodiment of the present invention.

The open-circuit detecting method for each of the receiving antennas according to the ninth embodiment of the present invention will be described. FIG. 17 is a flowchart showing an example of the open-circuit detecting method for each of the receiving antennas according to the ninth embodiment of the present invention. It is to be noted that in the receiving apparatus 303 for which each of the receiving antennas is subjected to the open-circuit detection by the open-circuit detecting method according to the ninth embodiment of the present invention, a battery or the like is set to the receiving apparatus 303 to turn the power supply unit 340 into a state in which the power supply unit 340 can supply the driving power. Furthermore, it is confirmed in advance that the receiving apparatus 303 operates normally while performing the self-diagnostic processing.

Figure 18:
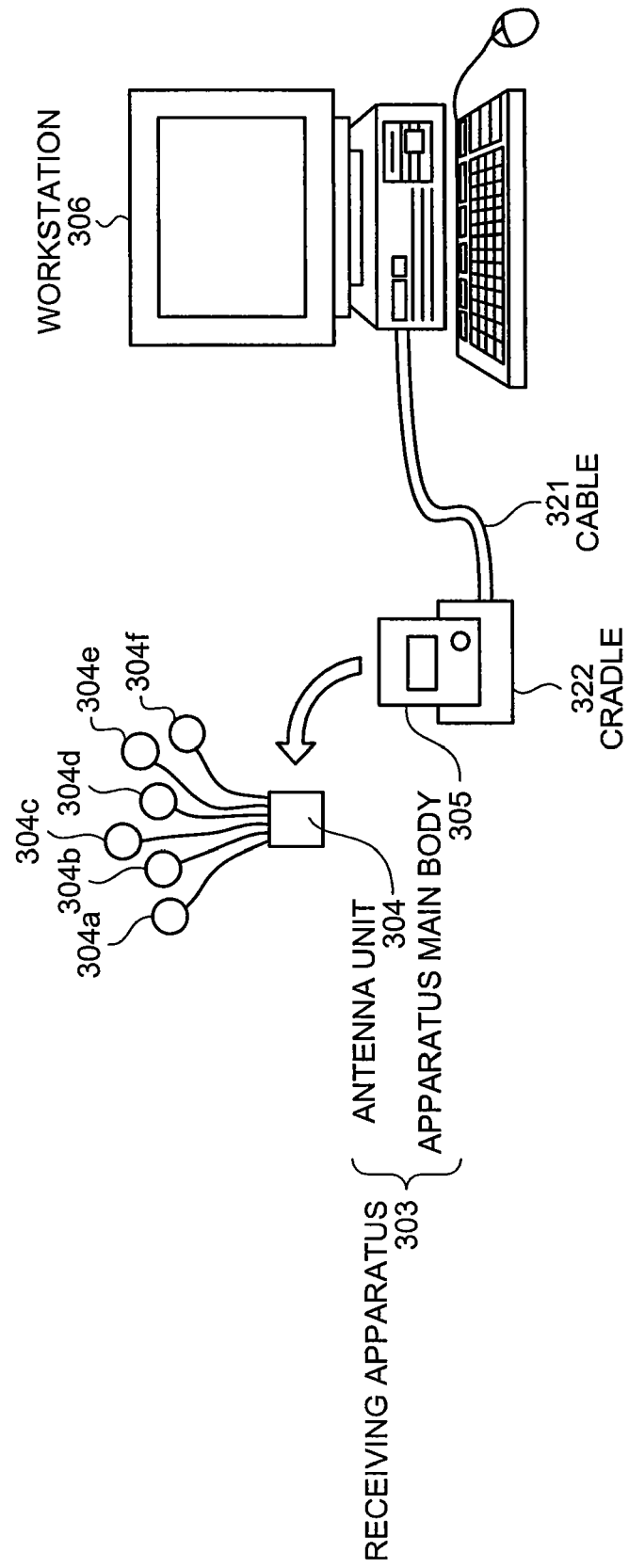
FIG. 18 is a pattern diagram for explaining a method of initializing an open-circuit detecting target receiving apparatus.

As shown in FIG. 17, the workstation 306 initializes the receiving apparatus 303 including the receiving antennas 304a to 304f to be subjected to the open-circuit detection (hereinafter, "open-circuit detecting-target receiving antennas"), and this receiving apparatus 303 is initialized as the receiving apparatus for carrying out the capsule endoscopy examination on the subject 1 (step S101). Specifically, as shown in FIG. 18, the antenna unit 304 is detached from the receiving apparatus 303, and the receiving apparatus 303 from which the antenna unit is detached, that is, the apparatus main body 305 is mounted on a cradle 322. The cradle 322 is connected to the workstation 306 through a cable 321. The workstation 306 is in a state in which an application for initializing the receiving apparatus 303 is booted, and the workstation 306 initializes the apparatus main body 305 based on the application.

The apparatus main body 305 thus initialized is detached from the cradle 322, and the antenna unit 304 is connected to the apparatus main body 305, thereby forming the receiving apparatus 303 (step S102). This receiving apparatus 303 is in a state in which the receiving apparatus 303 has been initialized, and information (e.g., a patient name, a patient ID, and an examination date) on the subject 1, for example, is registered in the receiving apparatus 303.

Thereafter, the monitor device 309 is connected to this receiving apparatus 303 through the cable 308 (step S103), and an operation check is performed on this monitor device 309 connected to the receiving apparatus 303 (step S104). Specifically, the control unit 339 of the receiving apparatus 303 is instructed to carry out the operation check on the monitor device 309 by operating the input unit 336. In this case, the operation check unit 339a diagnoses whether the display unit 397 of the monitor device 309 can monitor-display the image data generated by the signal processing circuit 334. The control unit 339 causes a diagnosis result of the operation check unit 339a with respect to the monitor device 309 to be displayed on the display unit 337. The user checks the diagnosis result with respect to the monitor device 309 displayed on the display unit 337, whereby the user can confirm whether the monitor device 309 can monitor-display the image data acquired by the receiving apparatus 303. Alternatively, at this operation check step S104, not only the operation check on the monitor device 309 but also the self-diagnostic processing on the receiving apparatus 303 can be performed.

Next, it is detected whether an open-circuit occurs to each of the receiving antennas of the receiving apparatus 303 to which the monitor device 309 confirmed to operate normally (confirmed to be able to monitor-display the image data) at this operation check step S104. Specifically, one open-circuit detecting-target receiving antenna is selected from among the receiving antenna 304a to 304f connected to the antenna unit 304 of this receiving apparatus 303 (step S105). The test radio signal is transmitted from the open-circuit detecting device to the selected, open-circuit-detection-target receiving antenna (step S106). In this case, as shown in, for example, FIG. 19, the open-circuit detecting device 310 is made closer to the receiving antenna 304a selected as the open-circuit detecting-target receiving antenna, and the test radio signal from the open-circuit detecting device 310 is turned into such a state as to be received only by the open-circuit detecting-target receiving antenna 304a. Moreover, the open-circuit detecting device 310 transmits the test radio signal including the desired test image designated in advance by the input operation performed by the input unit 311 to such a receiving antenna 304a for predetermined time.

It is to be noted that the time for transmitting the test radio signal is long enough for the monitor device 309 to display this test image if the receiving apparatus 303 acquires the test image through the receiving antenna to which no open-circuit occurs. Further, if the test image is already known to the user, i.e., the user recognizes in what display content the test image is transmitted by the test radio signal, the open-circuit detecting device 310 can transmit, as the desired test image, either the natural image or the pattern image.

It is determined whether the test image thus transmitted by open-circuit detecting device 310 is monitor-displayed on the monitor device 309 (step S107). Specifically, as shown in FIG. 19, if no open-circuit occurs between this receiving antenna 304a and the receiving apparatus 303, the test radio signal transmitted from the open-circuit detecting device 310 to the open-circuit detecting-target receiving antenna 304a is received by the receiving apparatus 303 through this receiving antenna 304a. In this case, the receiving apparatus 303 demodulates the test radio signal thus received into an image signal, acquires image data on the test signal based on the acquired image signal, and transmits this image data to the monitor device 309 through the cable 308. The monitor device 309 displays a test image P on the display unit 397 based on the image data received from the receiving apparatus 303. Accordingly, by confirming that the test image P is displayed on the display unit 397 of the monitor device 309 (step S107, Yes), the user can determine that no open-circuit occurs to the open-circuit detecting-target receiving antenna 304a at real time (step S108).

On the other hand, the test radio signal transmitted from the open-circuit detecting device 310 to the open-circuit detecting-target receiving antenna 304a is not received by this receiving apparatus 303 if an open-circuit occurs between this receiving antenna 304a and the receiving apparatus 303. In this case, the receiving apparatus 303 cannot acquire the test image included in the test radio signal. Due to this, the monitor device 309 does not display this test image on the display unit 397. Accordingly, by conforming that the test image is not displayed on the display unit 397 of the monitor device 309 (step S107, No), the user can determine that an open-circuit occurs to the open-circuit detecting-target receiving apparatus 304a (the open-circuit-detection-target receiving apparatus 304a is in an open-circuit state) at real time (step S109).

Thereafter, if the open-circuit detection is not completed with respect to all the receiving antennas 304a to 304f which the receiving apparatus 303 includes (step S110, No), the processing steps at and after the step S105 is repeated. In this case, one open-circuit detecting-target receiving antenna is selected from among the receiving antennas 304b to 304f except for the receiving antenna 304a that has been already subjected to the open-circuit detection. The processing steps at and after the step S106 are repeatedly performed on this selected receiving antenna. If the open-circuit detection has been performed with respect to all the receiving antennas 304a to 304f of the receiving antenna 303 in this manner (step S110, Yes), it is possible to detect whether an open-circuit occurs to each of the receiving antennas 304a to 304f.

If an open-circuit occurs to none of the receiving antennas 304a to 304f that have been subjected to the open-circuit detection, it is possible to determine that the receiving apparatus 303 including such receiving antennas 304a to 304f is in a normal state in which the receiving apparatus 303 can normally receive the radio signal from the capsule endoscope 302. Thereafter, the subject 1 is allowed to carry this receiving apparatus 303 in the normal state, whereby the capsule endoscopy examination can be promptly carried out on the subject 1.

If it is confirmed that an open-circuit occurs to one of the receiving antennas 304a to 304f, it can be determined that the receiving apparatus 303 including such receiving antennas 304a to 304f is in an abnormal state in which the receiving antenna 303 cannot normally receive the radio signal from the capsule endoscope 302. In this case, it can be determined that the abnormal state of the receiving apparatus 303 results from the open-circuit that occurs to one receiving antenna, and the receiving antenna to which the open-circuit occurs can be easily identified. Therefore, by replacing the receiving antenna to which the open-circuit occurs by a normal receiving antenna to which no open-circuit occurs, the receiving apparatus 303 in this abnormal state can be returned into the normal state. As a result, by allowing the subject 1 to carry the receiving apparatus 303 thus returned into the normal state, the capsule endoscopy examination can be instantly performed on the subject 1.

With the open-circuit detecting method according to the ninth embodiment of the present invention, the test image P included in the test radio signal transmitted from the open-circuit detecting device 310 can be displayed on the display unit 337 of the receiving apparatus 303 in place of the monitor device 309. In this case, there is no need to connect the monitor device 309 to the receiving apparatus 303, and the open-circuit detection can be performed with respect to the receiving antennas using this receiving apparatus 303 and the open-circuit detecting device 310. In this case, it suffices that the processing steps at and after the step S105 are performed on the receiving apparatus 303 on which the self-diagnostic processing and the steps S101 and S102 have been performed.

Specifically, as shown in FIG. 20, the open-circuit detecting device 310 is made closer to the receiving antenna 304a selected as the open-circuit detecting target from among the receiving antennas 304a to 304f. Furthermore, the test radio signal from this open-circuit detecting device 310 is transmitted to this receiving antenna 304a for predetermined time. If the test image P acquired by the receiving apparatus 303 based on this test radio signal is displayed on the display unit 337, then it can be determined that no open-circuit occurs to the receiving antenna 304a to which this test radio signal is transmitted. If this test image P is not displayed on the display unit 337, it can be determined that an open-circuit occurs to the receiving antenna 304a to which this test radio signal is transmitted. By repeating such open-circuit detection with respect to the remaining receiving antenna 304b to 304f, the open-circuit detection can be performed with respect to all the receiving antennas 304a to 304f.

In the ninth embodiment of this invention, the receiving apparatus 303 is initialized to register the information on the subject 1 in the receiving apparatus 303 so as to perform the open-circuit detection with respect to the receiving antennas. However, the present invention is not limited thereto. Alternatively, the receiving apparatus 303 can be initialized by registering information on a dummy subject set for the open-circuit detection, e.g., a dummy patient name, a dummy patient ID, and an open-circuit detecting date in the receiving apparatus 303.

Moreover, the test image transmitted to the receiving apparatus 303 by the open-circuit detection can be stored in the storage unit 335 of the receiving apparatus 303 or deleted by the control unit 339 after the test image is displayed on the monitor device 309 or the display unit 337.

As stated so far, in the ninth embodiment of the present invention, the receiving apparatus is connected to the portable monitor device through the cable, and the image data acquired by this receiving apparatus is displayed on the monitor device at real time. The test radio signal is transmitted from the open-circuit detecting device to each of the receiving antennas of this receiving apparatus for the predetermined time. If the test image included in this test radio signal is not displayed on this monitor device, it is determined that an open-circuit occurs to the receiving antenna to which this test radio signal is transmitted. Therefore, it is possible realize the open-circuit detecting method as follows. It can be determined whether the receiving apparatus is in the normal state in which the receiving apparatus can normally receive the radio signal from the capsule endoscope without the need to connect the receiving apparatus to the workstation that displays the image picked up by the capsule endoscope. Moreover, if it is determined that this receiving apparatus is in the abnormal state in which the receiving apparatus cannot normally receive the radio signal from the capsule endoscope, it can be determined that the abnormal state of this receiving apparatus results from the open-circuit that occurs to the receiving antenna. Furthermore, the receiving antenna to which the open-circuit occurs can be easily detected from among the receiving antennas.

The open-circuit detecting method according to the ninth embodiment exhibits the following advantages. It can be inspected whether the receiving apparatus is in the normal state in which the receiving apparatus can normally receive the radio signal from the capsule endoscope without the need to connect the receiving apparatus to the workstation that displays the image picked up by the capsule endoscope. Moreover, if it is determined that this receiving apparatus is in the abnormal state in which the receiving apparatus cannot normally receive the radio signal from the capsule endoscope, the receiving antenna that causes the abnormal state of the receiving apparatus can be easily detected from among the receiving antennas.

Moreover, by transmitting the test radio signal to the open-circuit detecting-target receiving antenna, it can be confirmed at real time whether an open-circuit occurs to this receiving antenna. It is, therefore, possible to reduce time required since the open-circuit detection is performed with respect to the receiving antenna until the subject for the capsule endoscopy examination is allowed to carry the normal receiving apparatus. The receiving apparatus in the normal state necessary for the capsule endoscopy examination can be easily prepared.

Moreover, it is possible to easily detect and identify the receiving antenna to which an open-circuit occurs from among the receiving antennas which the receiving apparatus includes. Therefore, the receiving antenna to which the open-circuit occurs can be easily replaced by a normal receiving antenna, and the receiving apparatus determined to be in the abnormal state due to the open-circuit that occurs to the receiving antenna can be easily returned into the normal state.

Furthermore, if the receiving apparatus is constituted to display the image data acquired through the receiving antenna on the display unit of the receiving apparatus at real time, the test radio signal is transmitted to each of the receiving antennas of the receiving apparatus including such a display unit for the predetermined time. By doing so, it is possible determine whether this receiving apparatus is in a normal state without the need to connect the monitor device to the receiving apparatus. Moreover, if this receiving apparatus is determined to be in the abnormal state, then it can be determined that the abnormal state of this receiving apparatus results from the open-circuit that occurs to one receiving antenna, and the receiving antenna to which the open-circuit occurs can be easily detected and identified from among the receiving antennas.

The first to ninth embodiments described in the specification of the present application can be carried out by combinations thereof. For example, the open-circuit detection can be performed with respect to the receiving antennas using the open-circuit detecting device 310 and the receiving apparatus 2 or 102. Further, the receiving apparatus 2 or 102 can be connected to the monitor device 309, and the result of the open-circuit detection with respect to the receiving antennas processed by the receiving apparatus 2 or 102 can be displayed on the monitor device 309. Alternatively, the control unit 339 of the receiving apparatus 303 can include an open-circuit detecting processor corresponding to the open-circuit detecting processor C2a, and the control unit 339 including such an open-circuit detecting processor can detect whether an open-circuit occurs to each of the receiving antennas almost similarly to the fourth to eighth embodiments. In another alternative, the antenna unit 304 of the receiving apparatus 303 can include an open-circuit detecting circuit corresponding to the open-circuit detecting circuit 23 and a changeover switch (corresponding to the changeover switch 22) for switching the connection state in which this open-circuit detecting circuit is connected to one of the receiving antennas 304a to 304f. Furthermore, the antenna unit 304 can detect whether an open-circuit occurs to each of the receiving antennas using this open-circuit detecting circuit. In this case, the switching control circuit 333 further controls the changeover switch to switch over the connection state between the open-circuit detecting circuit and one of the receiving antennas 304a to 304f. Moreover, the control unit 339 can detect whether an open-circuit occurs to each of the receiving antennas based on the detection signal S6 from the open-circuit detecting circuit.

INDUSTRIAL APPLICABILITY

As described so far, the present invention is effective if the radio signal including the image data picked up by the capsule endoscope inserted into the organ of the subject is received from the capsule endoscope inserted into this subject. The receiving apparatus is particularly suited as the receiving apparatus that can detect whether an open-circuit occurs between the receiving antenna and the receiving apparatus for receiving the radio signal from the capsule endoscope in the body of the subject (that is, whether an open-circuit occurs to the feeder that connects the receiving apparatus to the receiving antenna) easily within short time.

The invention claimed is:

1. A receiving apparatus for receiving transmitted information transmitted from a moving transmitting apparatus through a selected and switched feeder and a receiving antenna, the receiving apparatus comprising:

a selecting/switching unit that selects and switches one of a plurality of feeders connected to a plurality of receiving antennas, respectively;

a detective selecting/switching unit that branches the plurality of feeders near the selecting/switching unit, respectively, and selects and switches one of the branched feeders;

a grounding unit, provided between each of the feeders and each of the receiving antennas, that grounds each of the feeders;

an open-circuit detecting unit that applies a direct-current voltage to the feeder selected and switched by the detective selecting/switching unit through a constant-current source, and that detects whether an open-circuit occurs in the selected and switched feeder based on whether a voltage of the feeder is equal to a ground voltage; and a control unit that controls the detective selecting/switching unit to perform selection and switching, and makes the open-circuit detecting unit to detect an open-circuit synchronously with the control over the selection and switching of the detective selecting/switching unit.

2. The receiving apparatus according to claim 1, wherein each of the receiving antennas is an open receiving antenna, each of the feeders and each of the receiving antennas are connected to each other by a transformer balun, and a feeder-side of the transformer balun is grounded.

3. The receiving apparatus according to claim 1, wherein each of the receiving antennas is an open receiving antenna, each of the feeders and each of the receiving antennas are connected to each other by a short-circuit element, and one end of the short-circuit element is grounded.

4. The receiving apparatus according to claim 1, wherein each of the receiving antennas is a loop antenna, and one end at which each of the feeders is connected to each of the receiving antennas is grounded.

5. The receiving apparatus according to claim 1, wherein each of the feeders is a coaxial cable, and an external conductor is grounded.

6. The receiving apparatus according to claim 1, wherein the control unit performs a control to display by outputting a result of the open-circuit detection.

7. A receiving apparatus for receiving transmitted information transmitted from a moving transmitting apparatus through a selected and switched feeder and a receiving antenna, the receiving apparatus comprising:

a selecting/switching unit that selects and switches one of a plurality of feeders connected to a plurality of receiving antennas, respectively;

a detective selecting/switching unit that branches the plurality of feeders near the selecting/switching unit, respectively, and selects and switches one of the branched feeders;

an open-circuit detecting unit, provided between each of the feeders and each of the receiving antennas, that detects whether an open-circuit occurs in the selected and switched feeder by applying a direct-current voltage; and a control unit that controls the detective selecting/switching unit to perform selection and switching, and makes the open-circuit detecting unit to detect an open-circuit synchronously with the control over the selection and switching of the detective selecting/switching unit.

* * * * *